United States Patent
Nakayama et al.

(10) Patent No.: US 8,685,082 B2
(45) Date of Patent: Apr. 1, 2014

(54) BASE MATERIAL FOR FORMING VALVED LUMEN SHAPE TISSUE, METHOD FOR PRODUCING VALVED LUMEN SHAPE TISSUE, AND VALVED ARTIFICIAL BLOOD VESSEL

(75) Inventors: Yasuhide Nakayama, Suita (JP); Tomonori Oie, Osaka (JP)

(73) Assignee: National Cerebral and Cardiovascular Center, Osaka (JP)

( * ) Notice: Subject to any disclaimer, the term of this patent is extended or adjusted under 35 U.S.C. 154(b) by 123 days.

(21) Appl. No.: 13/390,480

(22) PCT Filed: Nov. 16, 2011

(86) PCT No.: PCT/JP2011/076372
§ 371 (c)(1),
(2), (4) Date: Feb. 14, 2012

(87) PCT Pub. No.: WO2012/067137
PCT Pub. Date: May 24, 2012

(65) Prior Publication Data
US 2012/0191179 A1    Jul. 26, 2012

(30) Foreign Application Priority Data

Nov. 18, 2010  (JP) ................................ 2010-257821
Dec. 27, 2010  (JP) ................................ 2010-289241
Sep. 9, 2011    (JP) ................................ 2011-197657

(51) Int. Cl.
*A61F 2/06*    (2013.01)
(52) U.S. Cl.
USPC ..................... 623/1.49; 623/23.68; 623/23.72; 264/222; 264/250; 264/255; 264/275; 264/313; 425/2; 425/3; 425/179; 425/184; 425/468; 249/98; 249/124; 249/126; 249/139; 249/156; 249/163

(58) Field of Classification Search
USPC ......... 425/2, 3, 175, 179, 182, 184, 186, 468, 425/808, DIG. 33; 249/98–101, 124–127, 249/139, 155–157, 163–167; 264/222, 225, 264/250, 255, 275, 313; 433/34; 623/1.49, 623/23.64, 23.7, 23.72
See application file for complete search history.

(56) References Cited

U.S. PATENT DOCUMENTS 2,677,149 A * 5/1954 Fineran ........................... 249/96
3,320,972 A * 5/1967 High et al. ..................... 137/844
(Continued)

FOREIGN PATENT DOCUMENTS

JP    62105613 A  *  5/1987    ............. B29C 43/18
JP    62257821 A  *  11/1987   ............. B29C 45/37
(Continued)

OTHER PUBLICATIONS

Anita Mol, PhD et al., "Autologous Human Tissue-Engineered Heart Valves", Jul. 4, 2006, Circulation 1-152-158.

*Primary Examiner* — Dimple Bodawala
(74) *Attorney, Agent, or Firm* — Wenderoth, Lind & Ponack, L.L.P.

(57) ABSTRACT

The present invention provides a base material which can be formed into valved lumen shape tissue having an ampulla and a leaflet consisting of body tissue. Specifically, the base material includes a first column 5 that forms an upstream tubular section 4 of a blood vessel 3, a second column 7 that forms a downstream tubular section 6 of the blood vessel 3, a plurality of bulges 10 for forming an ampulla 8 and a leaflet 9 of the blood vessel 3, and engagement means 11 that causes the bulge 10 to engage the first column 5 and/or the second column 7. The engagement means 11 includes recesses 15a and 15b in axial end surfaces of one or both of the first column 5 and the second column 7, and an engagement section 18 that overhangs from a bulge body 17 and engages the recesses. An outer peripheral surface of the body 17 of the bulge 10 is an ampulla forming surface 20, and a gap provided between the bulge body 17 and the first column 5 and/or the second column 7 is a leaflet forming section 22.

18 Claims, 25 Drawing Sheets

(56) References Cited

U.S. PATENT DOCUMENTS

| | | | |
|---|---|---|---|
| 3,655,306 A * | 4/1972 | Ross et al. | 425/521 |
| 4,210,478 A * | 7/1980 | Shoney | 156/242 |
| 4,386,045 A * | 5/1983 | Vaisanen | 264/249 |
| 4,737,219 A * | 4/1988 | Taller et al. | 156/215 |
| 5,116,564 A * | 5/1992 | Jansen et al. | 264/255 |
| 5,217,671 A * | 6/1993 | Moriuchi et al. | 264/313 |
| 6,491,778 B1 * | 12/2002 | Fenton et al. | 156/184 |
| 6,561,788 B1 * | 5/2003 | Gaudoin | 425/522 |
| 6,818,162 B1 * | 11/2004 | Hoffman et al. | 264/46.4 |
| 7,736,571 B2 * | 6/2010 | Trapp | 264/293 |
| 8,562,671 B2 * | 10/2013 | Neuenschwander | 623/1.49 |
| 2004/0254640 A1 * | 12/2004 | Sutherland et al. | 623/2.13 |
| 2006/0271167 A1 * | 11/2006 | Knight | 623/1.26 |
| 2010/0168832 A1 * | 7/2010 | Neuenschwander | 623/1.1 |
| 2011/0270406 A1 * | 11/2011 | Weitzner et al. | 623/23.7 |
| 2011/0307070 A1 * | 12/2011 | Clerc et al. | 623/23.7 |

FOREIGN PATENT DOCUMENTS

| | | |
|---|---|---|
| JP | 2006-524119 | 10/2006 |
| JP | 2006-314601 | 11/2006 |
| JP | 2007-37764 | 2/2007 |
| JP | 2007-312821 | 12/2007 |
| JP | 2008-237896 | 10/2008 |
| JP | 2009-539439 | 11/2009 |
| JP | 2010-88625 | 4/2010 |
| JP | 2010-94476 | 4/2010 |
| WO | 2004/096100 | 11/2004 |
| WO | 2007/140964 | 12/2007 |
| WO | 2008/036588 | 3/2008 |

\* cited by examiner

BASE MATERIAL FOR FORMING VALVED LUMEN SHAPE TISSUE, METHOD FOR PRODUCING VALVED LUMEN SHAPE TISSUE, AND VALVED ARTIFICIAL BLOOD VESSEL

TECHNICAL FIELD

The present invention relates to a base material for forming valved lumen shape tissue such as a valved artificial blood vessel, a method for producing the valved lumen shape tissue using the base material, and a valved artificial blood vessel.

BACKGROUND ART

Generally, when foreign matter enters a deep position in a body, a capsule of connective tissue mainly consisting of fibroblasts and collagen is formed so as to cover the foreign matter, and isolates the foreign matter in the body. A method is disclosed using this self-protective reaction to form tubular tissue derived from a living body with living cells in a living body (see Patent Literatures 1 to 4 and Non-patent Literature 1).

These literatures disclose methods for forming tissue derived from a living body having a relatively simple structure, and further, production is desired of tissue derived from a living body having a complicated structure with an ampulla and a leaflet, such as an aortic sinus (Valsalva sinus) of an aorta. The aortic sinus (Valsalva sinus) includes an ampulla with a blood vessel wall expanding radially outward, and a plurality of leaflets that open/close a blood vessel inside and on an upstream side of the ampulla, and the ampulla functions as an escape path for blood when a valve opens, and functions as a reservoir for the blood when the valve closes.

As means for producing a valved artificial blood vessel including such an ampulla and a leaflet, Patent Literature 5 discloses an artificial heart valve containing biocompatible block copolymer and a scaffold for a blood vessel structure.

In the technique disclosed in Patent Literature 5, first, fibers are deposited on a valve model including a plurality of model parts by electospinning to construct a mesh structure. Then, the model parts are released from the mesh structure to complete a scaffold of the valve model. The scaffold has a mesh-like structure formed by polymer fibers. Cells (endothelial cells or myofibroblasts) are cultured on the scaffold, and thus the cells grow in the mesh structure to form a valved artificial blood vessel.

CITATION LIST

Patent Literature

Patent Literature 1: Japanese Patent Laid-Open No. 2007-312821
Patent Literature 2: Japanese Patent Laid-Open No. 2008-237896
Patent Literature 3: Japanese Patent Laid-Open No. 2010-094476
Patent Literature 4: Japanese Patent Laid-Open No. 2006-314601
Patent Literature 5: National Publication of International Patent Application No. 2009-539439

Non Patent Literature

Non-patent Literature 1: Antia Mol, PhD et al, "Autologous Human Tissue-Engineered Heart Valves" Jul. 4, 2006, Circulation, 1-152 to 158

SUMMARY OF INVENTION

Technical Problem

However, as shown in FIG. 36, in the scaffold 101 in Patent Literature 5, three leaflets are continuously formed between an end surface of a first model part and three end surfaces of a second model part, and this requires an extra step of cutting the leaflets into three pieces (see paragraph [0045] in Patent Literature 5).

The present invention has an object to provide a base material which can be formed into valved lumen shape tissue having an ampulla and a leaflet consisting of body tissue, a method for producing the valved lumen shape tissue using the base material, and a valved artificial blood vessel.

Solution to Problem

A base material for forming valved lumen shape tissue according to the present invention is a base material that is placed in an environment with a body tissue material to form film-like tissue on a surface thereof, and from which the tissue is released to form valved lumen shape tissue, including: a first column that forms an upstream tubular section of the lumen shape tissue; a second column that forms a downstream tubular section of the lumen shape tissue; a plurality of bulges for forming an ampulla provided between the upstream tubular section and the downstream tubular section and having a lumen shape tissue wall expanding radially outward, and a leaflet that protrudes radially inward in the ampulla and is openable/closable in a flow direction; and engagement means that causes the bulge to removably engage the first column and/or the second column, wherein the engagement means includes a recess that is formed in an axial end surface of one or both of the first column and the second column and is axially recessed, and an engagement section that overhangs radially inward from a body of the bulge to engage the recess, and thus regulates radial, circumferential, and axial displacement of the bulge with respect to the first column and the second column, and an outer peripheral surface of the body of the bulge is an ampulla forming surface, and a gap provided between the bulge body and the first column and/or the second column is a leaflet forming section. The first column and the second column have outer peripheral surfaces that are forming surfaces of the lumen shape tissue such as a blood vessel, and preferably mostly have a cylindrical shape.

Such a base material for forming valved lumen shape tissue is placed in an environment with a body tissue material for a predetermined period (placement step), then the base material for forming valved lumen shape tissue covered with tissue is taken out from the environment (taking-out step), the base material for forming valved lumen shape tissue is taken out from the tissue (separation step), and thus the valved lumen shape tissue having an ampulla and a leaflet consisting of body tissue can be formed. In the separation step, when the base material for forming valved lumen shape tissue is taken out from the tissue formed around the base material, the base material can be disassembled and taken out, and thus can be easily drawn without damaging the tissue. As such, the formed valved lumen shape tissue can be applied to a blood vessel having an ampulla and a leaflet such as aortic sinus (Valsalva sinus), pulmonary artery sinus, carotid sinus, superior petrosal sinus, transverse sinus, pituitary sinus, or the like.

The engagement section of the bulge overhangs radially inward from the bulge body. Thus, the engagement section engages the recess in the first column and/or the second column, and thus the bulge body protrudes from surfaces of the first column and the second column. The outer peripheral surface of the bulge body is the ampulla forming surface, and the gap (leaflet forming section) provided between the bulge body and the first column and/or the second column can form a leaflet. Since the leaflet forming section can form one complete leaflet, the leaflet can be completed without cutting.

The recess of the engagement means may be provided in any one of the first column and the second column, but recesses may be provided in both the first column and the second column and placed on each other, and the engagement section of the bulge may be housed in the recesses.

The engagement means is preferably configured so that the engagement section is housed in the recess and axially held between the first column and the second column for engagement. In the separation step of taking out the base material for forming valved lumen shape tissue from the tissue, the first column and the second column are axially disassembled from the bulges and taken out from a lumen of the tissue, and then the plurality of bulges are taken out from the lumen. Then, all base materials can be axially drawn without damaging the tissue formed therearound.

Securing means that integrally secures the first column, the second column, and the bulge is preferably provided. A unit of the first column, the second column, and the bulge integrated together can be stably placed in the environment with a body tissue material.

The securing means may have various aspects. As one aspect, the securing means includes a through hole formed to axially pass through centers of the first column and the second column, and a through shaft that is inserted through the through hole to integrally secure the engagement section of the bulge, the first column, and the second column. The through shaft may be a rod, a thread, or a magnet as long as it can be inserted through the through hole. For example, the securing means may include a male thread provided on an outer periphery of the through shaft, and a female thread formed on a peripheral surface of the through hole in the first column and/or the second column so as to be screwed onto the male thread. If the male thread is threaded into the female thread in the through hole, the engagement section of the bulge, the first column, and the second column can be integrally secured.

Also, as a second aspect, the securing means may include a male thread formed on one of the first column and the second column, and a female thread formed on the other of the first column and the second column so as to be screwed onto the male thread. The male thread on one column is screwed onto the female thread on the other column, thereby integrally securing the columns and the bulge.

As a third aspect, the securing means may include a magnetic material placed on one of the first column and the second column, and a magnetized material that is placed on the other of the first column and the second column and attracted to the magnetic material. The magnetized material on the other column is attracted to the magnetic material on one column, thereby integrally securing the columns and the bulge.

As a fourth aspect, the securing means may include an engagement pawl placed on one of the first column and the second column, and an engagement hole formed in the other of the first column and the second column so as to removably engage the engagement pawl. The engagement pawl on one column engages the engagement hole in the other column, thereby integrally securing the columns and the bulge.

The bulge body preferably includes a penetration hole that provides communication between a radially outer side of the bulge body and the leaflet forming section, and causes the tissue to easily penetrate the leaflet forming section. The tissue can easily penetrate the leaflet forming section, thereby speeding up formation of a thick leaflet. One penetration hole may be provided or a plurality of penetration holes may be provided for more penetration of tissue.

A third column connected to an outer surface of one or more bulge bodies is provided, and an outer peripheral surface of the third column may be a blood vessel forming surface branching off from the ampulla. For example, for a blood vessel of heart, a blood vessel formed around the third column may be coronary artery. The third column is preferably removable from the outer surface of the bulge body.

In the present invention, the "body tissue material" is a material required for forming desired tissue derived from a living body, and includes, for example, animal cells such as fibroblasts, smooth muscle cells, endothelial cells, stem cells, ES cells, or iPS cells, various proteins (collagen or elastin), saccharides such as hyaluronic acid, other cell growth factors, or various physiologically active substances in the living body such as cytokine. The "body tissue material" includes materials derived from mammalian such as human, dog, cow, pig, goat or sheep, birds, fish, and other animals, and artificial materials comparable thereto. Also, "in the environment with a body tissue material" refers to in a living body of animals or an artificial environment containing a body tissue material outside a living body of animals.

A body tissue formation observation apparatus may be provided, at an end of the first column, including photographing means that photographs the leaflet forming section, and transmission means that transmits an image photographed by the photographing means to the outside of the environment with a body tissue material.

According to this configuration, in the placement step, a formation state of tissue can be observed by the body tissue formation observation apparatus while film-like tissue is being formed around the base material for forming valved lumen shape tissue, and then the process can move to the taking-out step after it is confirmed that the tissue is sufficiently and reliably formed on the surface of the base material.

Further, since the photographing means is provided at the end of the first column, the leaflet forming section where the tissue is relatively not easily formed can be observed, and it can be determined that the tissue is formed on the outside of the bulge by just confirming that the tissue is formed on the leaflet forming section. In order for the tissue to be formed on the leaflet forming section, the tissue needs to penetrate the leaflet forming section while growing, and thus the tissue is relatively not easily formed on the leaflet forming section as compared to on the outside of the bulge.

Further, a region of the first column housing at least the photographing means of the body tissue formation observation apparatus is preferably made of a see-through material. According to this configuration, the tissue formed on the surface of the base material can be observed while the photographing means is being protected by the first column. The see-through material may include translucent silicone resin or translucent acrylic resin.

Further, the body tissue formation observation apparatus is preferably used intermittently by on/off operation from the outside of the environment with a body tissue material. According to this configuration, the intermittent use of the body tissue formation observation apparatus can reduce, for example, battery drain, and the body tissue formation observation apparatus can be used for a period sufficient for formation of the tissue. Further, the on/off operation from the outside of the environment includes on/off operation by magnetism, or on/off operation by sound waves or infrared rays.

The photographing means including a light source that applies a visible light, and a camera that receives and images the visible light reflected by the tissue can be used. The photographing means may photograph the tissue using X-rays, infrared rays, or ultrasound instead of the visible light, or apply an excitation light such as an ultraviolet ray to the tissue for fluorescent observation.

An auxiliary structure may be spaced radially outward from the outer surfaces of the first column and the second column. The base material having this configuration is placed in the environment, then the tissue is formed on the outer peripheral surfaces of the first column and the second column, and the tissue is also formed on the radially outside of the auxiliary structure, and the tissue is further formed to fill a gap between the first column and the second column, and the auxiliary structure. As such, using the auxiliary structure, thick tissue derived from a living body integrally including tubular inner layer tissue formed on the outer peripheral surfaces of the first column and the second column and an outer layer tissue formed on the outside of the auxiliary structure can be formed.

Further, it is preferable that the auxiliary structure includes auxiliary columns arranged around the first column and the second column, and the auxiliary columns are arranged at the same distance from and inclined to, or in parallel with the axes of the first column and the second column so that the auxiliary columns can be drawn axially with respect to the first column and the second column. According to this configuration, the auxiliary structure is separated from the first column and the second column, and then the auxiliary structure can be drawn from the tissue axially with respect to the first column and the second column. The auxiliary structure in which the auxiliary columns are arranged at the same distance from and inclined to the axes of the first column and the second column may be drawn from the tissue while being axially rotated. The auxiliary structure in which the auxiliary columns are arranged in parallel with the axes of the first column and the second column may be linearly drawn from the tissue.

The auxiliary structure may be integrated with the first column and/or the second column, and both may be physically cut to separate the auxiliary structure from the columnar structures in the separation step, or the auxiliary structure may be removably provided on the first column and/or the second column. The removable configuration does not cause a break of the base material, and thus the base material can be economically repeatedly reused.

Advantageous Effects of Invention

According to the base material for forming valved lumen shape tissue of the present invention, the base material for forming valved lumen shape tissue can be disassembled and taken out from the tissue formed around the base material, and thus can be easily drawn without damaging the tissue. Valved lumen shape tissue such as a valved artificial blood vessel having an ampulla and a leaflet consisting of body tissue can be formed.

With the gap (leaflet forming section) provided between the bulge body and the first column and/or the second column, one completed leaflet can be formed, thereby eliminating the need to cut the leaflet.

BRIEF DESCRIPTION OF DRAWINGS

FIG. 12(a) shows a valve being opened, and FIG. 12(b) shows the valve being closed.

DESCRIPTION OF EMBODIMENTS

As illustrated in first to twelfth embodiments, a base material for forming a valved artificial blood vessel 1 as valved lumen shape tissue of the present invention is placed in an environment with a body tissue material to form film-like tissue 2 on a surface thereof, the tissue 2 is released from the base material to form a valved artificial blood vessel 3.

First Embodiment

Figure 1:
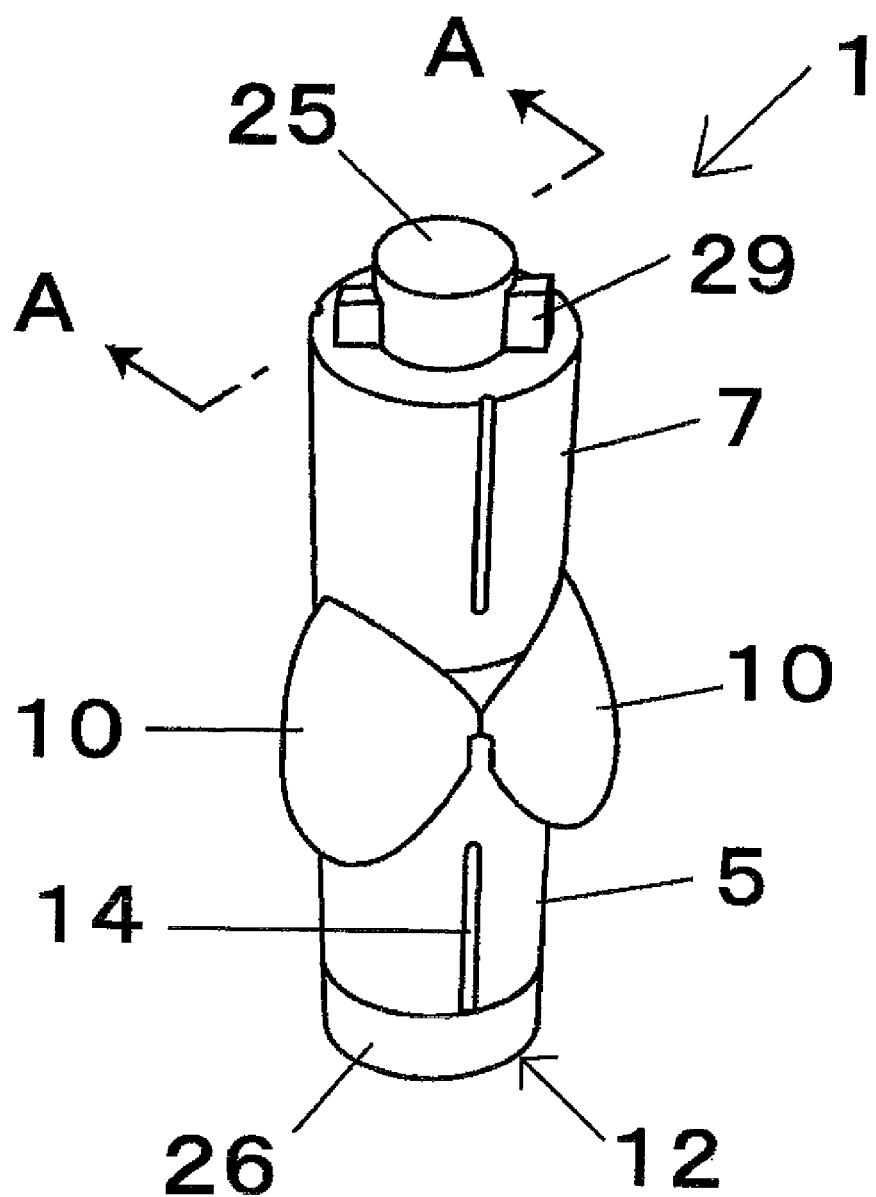
FIG. 1 is a perspective view of a base material for forming a valved artificial blood vessel according to a first embodiment.
Figure 2:
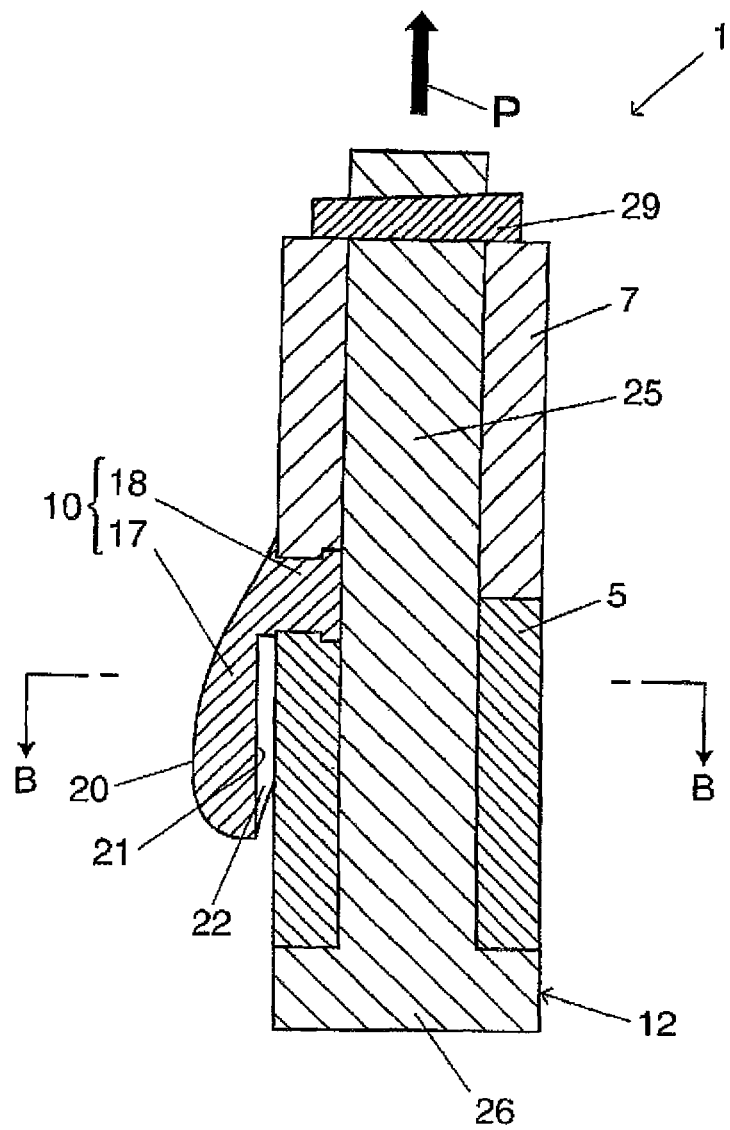
FIG. 2 is an A-A sectional view of FIG. 1.
Figure 10:
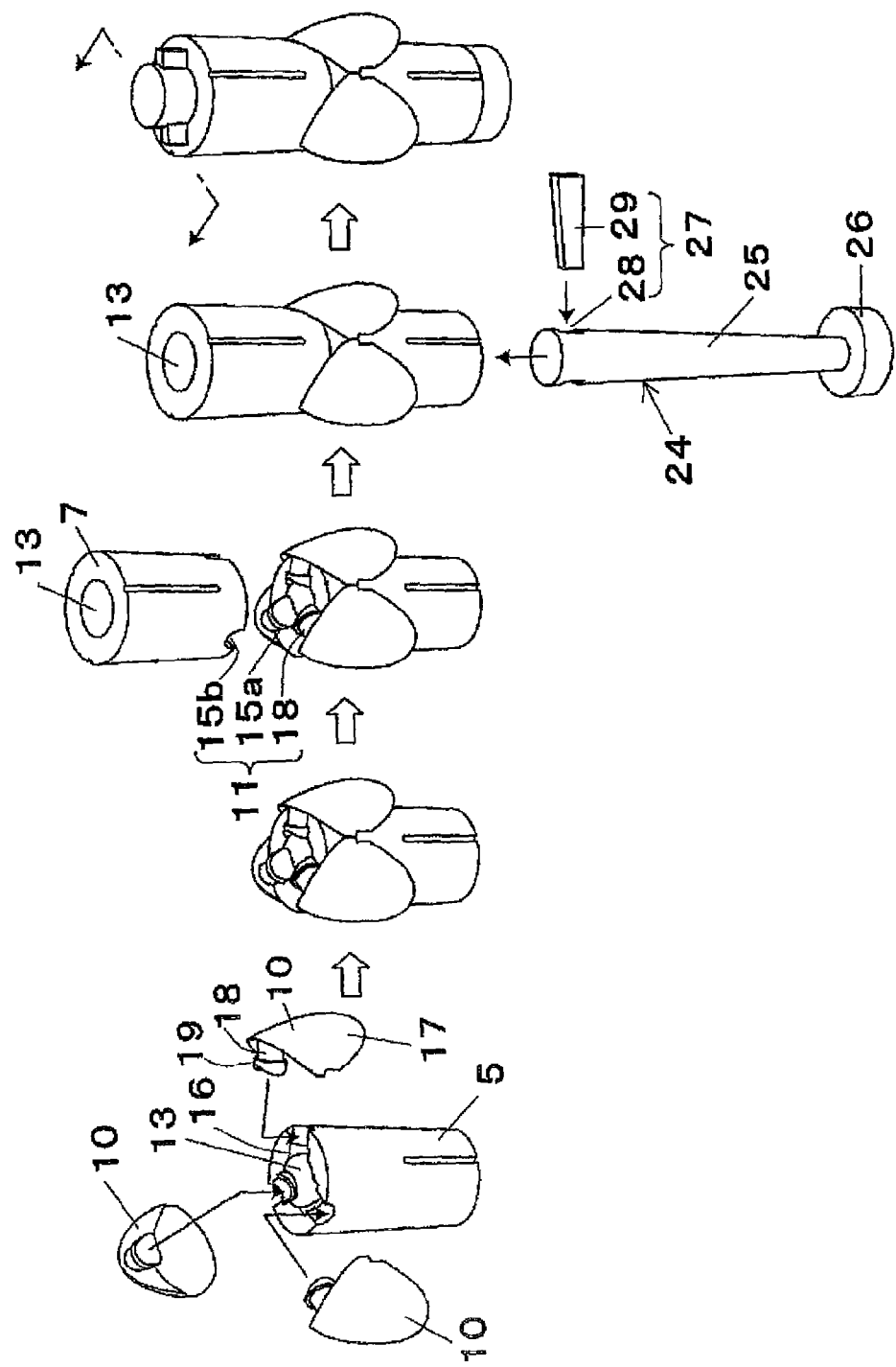
FIG. 10 is a view showing an assembling process of the base material for forming a valved artificial blood vessel.
Figure 11:
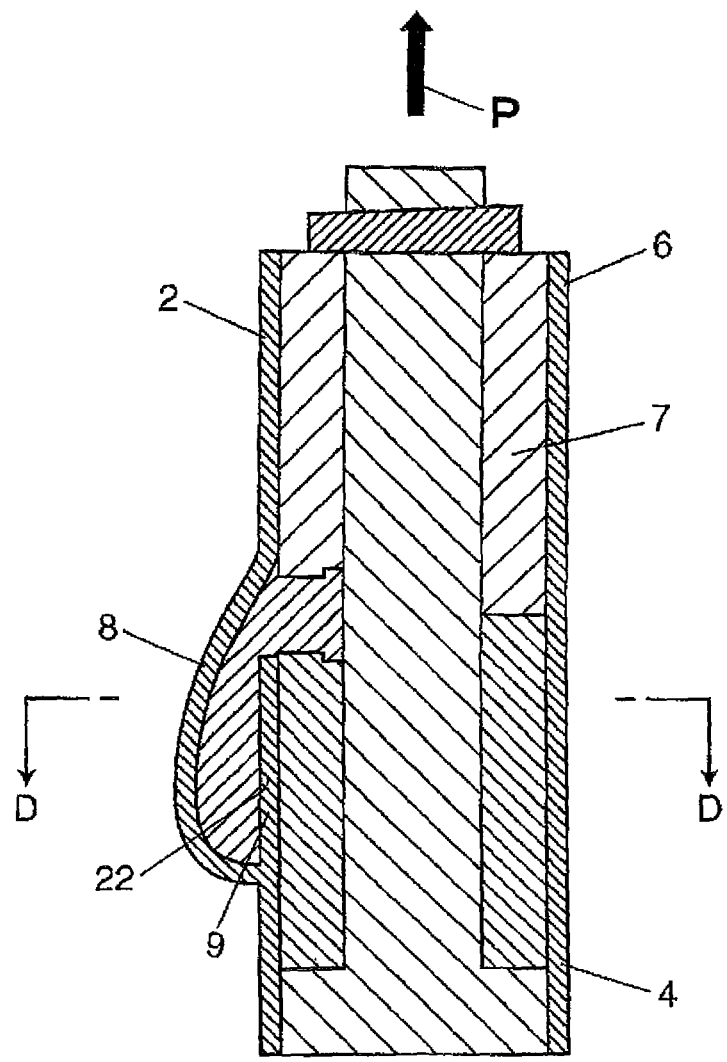
FIG. 11 is a vertical sectional view of the base material for forming a valved artificial blood vessel being covered with tissue.

As shown in FIGS. 1, 2 and 10, the base material for forming a valved artificial blood vessel 1 includes a first column 5 that forms an upstream tubular section 4 that is an upstream region in a blood flow direction of a blood vessel 3, a second column 7 that forms a downstream tubular section 6 that is a downstream region in the blood flow direction of the blood vessel 3, a plurality of bulges 10 for forming an ampulla 8 that is provided between the upstream tubular section 4 and the downstream tubular section 6 and has a blood vessel wall expanding radially outward, and a leaflet 9 that protrudes radially inward in the ampulla 8 and is openable/closable in the blood flow direction, engagement means 11 that causes the bulge 10 to removably engage the first column 5 and the second column 7, and securing means 12 that integrally secures the first column 5, the second column 7, and the bulge 10.

The base material for forming a valved artificial blood vessel 1 is preferably made of resin having strength (hardness) such that the resin is not significantly deformed when embedded into a living body, having chemical stability, resistant to load such as sterilization, producing no or less effluent that stimulates the living body, and for example, silicone resin or acrylic resin can be exemplified. Using an elastic body such as silicone resin tends to increase a thickness of the tissue 2 formed on a surface thereof. Thus, a surface of the entire base material for forming a valved artificial blood vessel 1, or at least surfaces of the first column 5, the second column 7, and the bulge 10 that come into contact with the tissue 2 are preferably made of an elastic body such as silicone resin.

Surface roughness (Ra) of the base material for forming a valved artificial blood vessel 1 is preferably 0.1 to 50 μm. With the surface roughness (Ra) of 50 μm or less, the tissue 2 formed around the base material can be thicker, thereby increasing self-standing of the blood vessel 3 and facilitating anastomosis with the blood vessel in the living body. Even if the surface roughness (Ra) is about 0.1 μm close to that of a mirror surface, thick tissue 2 can be formed around the base material. In this embodiment, the surface roughness (Ra) of the base material 1 is 20 μm. Mean roughness (Ra) is "arithmetic mean roughness", and refers to "arithmetic mean roughness (Ra)" provided by JIS B 0601-1994 "surface roughness—definition".

The relationship between surface roughness (Ra) of the base material and the thickness of tissue formed on the surface was checked to find that the thickness of tissue formed on the base material surface having surface roughness (Ra) of 90 μm was 40.9±10.5 μm, the thickness of tissue formed on the base material surface having surface roughness (Ra) of 50 μm was 124.4±17.4 μm, and the thickness of tissue 2 formed on the base material surface having surface roughness (Ra) of 20 μm was 157.4±39.5 μm.

The first column 5 is a cylinder made of silicone resin, the second column 7 is a cylinder made of acrylic resin, and both have an outer diameter of 20 mm and an entire length of about 30 mm. A through hole 13 having a diameter of about 10 mm is formed in the center of each of the first column 5 and the second column 7.

The first column 5 and the second column 7 do not include a member protruding radially outward, and outer peripheral surfaces thereof form a tubular luminal surface of the artificial blood vessel 3. A plurality of axially extending shallow thin grooves 14 are formed in the surfaces of the first column 5 and the second column 7. With the thin grooves 14, air enters when the tissue 2 is drawn, and thus the tissue 2 can be easily drawn. Since outer diameters of the first column 5 and the second column 7 determine the thickness of the blood vessel 3, the diameters of the first column 5 and the second column 7 can be changed depending on a target thickness. Irregularities or a shell member may be provided on the surface of the base material 1 to further increase mechanical strength of the tissue derived from a living body.

A plurality of axially recessed recesses 15a and 15b are formed in mating end surfaces of the first column 5 and the second column 7. In this embodiment, three recesses 15a and three recesses 15b are formed to match the number of the leaflets 9, and formed in corresponding positions between the first column 5 and the second column 7. The recesses 15a and 15b each have an engagement groove 16 with a radially inward side being wide.

The bulge 10 is made of acrylic resin, and as shown in FIGS. 4 to 9, includes a bulge body 17, and an engagement section 18 overhanging radially inward from the bulge body 17. In this embodiment, three bulges 10 are provided to match the number of the leaflets 9. The engagement section 18 overhangs radially inward from the bulge body 17, and engages an overlapping region of the recess 15a in the first column 5 and the recess 15b in the second column 7, and the bulge body 17 protrudes from the surfaces of the first column 5 and the second column 7.

As shown in FIG. 10, the engagement section 18 has a shape complementary to the shape of the overlapping region of the recess 15a in the first column 5 and the recess 15b in the second column 7. Thus, the engagement section 18 prevents circumferential and axial displacement of the bulge 10 with respect to the first column 5 and the second column 7. The engagement section 18 has a wide section 19 having a radially inward tip enlarged in a flange shape. The wide section 19 fits in the engagement grooves 16 in the recesses 15a and 15b to prevent radial displacement of the bulge 10 with respect to the first column 5 and the second column 7.

Figure 3:
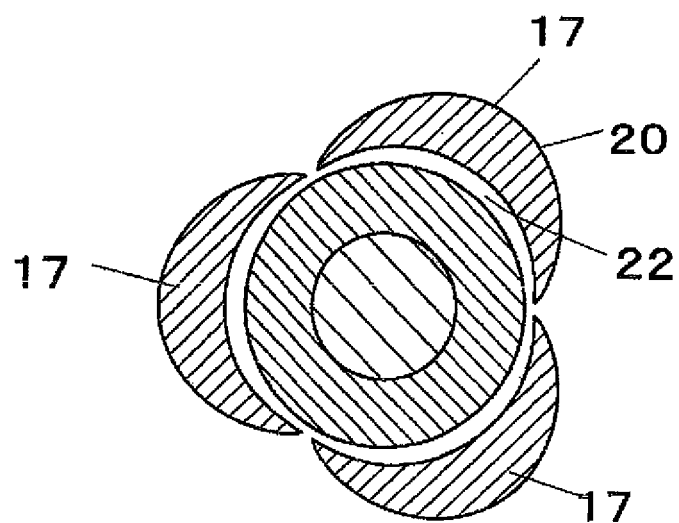
FIG. 3 is a B-B sectional view of FIG. 2.
Figure 4:
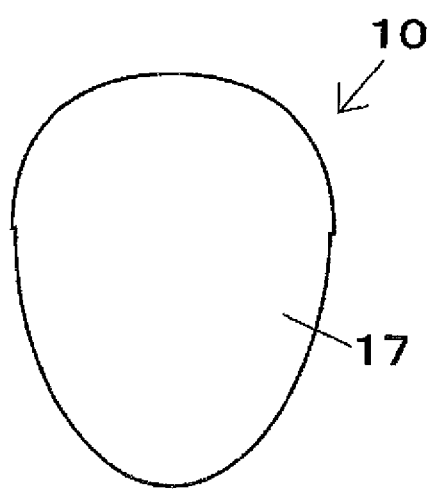
FIG. 4 is a front view of a bulge of the base material for forming a valved artificial blood vessel.
Figure 5:
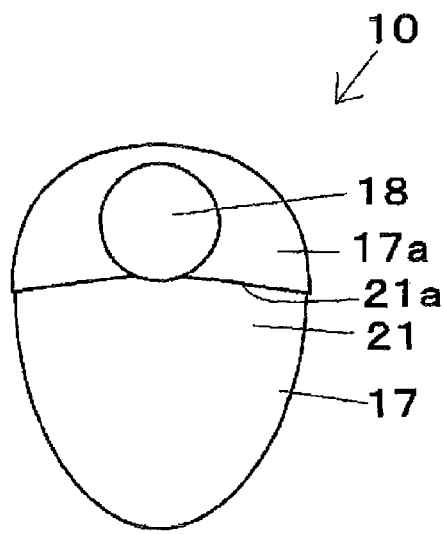
FIG. 5 is a back view of the bulge of the base material for forming a valved artificial blood vessel.
Figure 6:
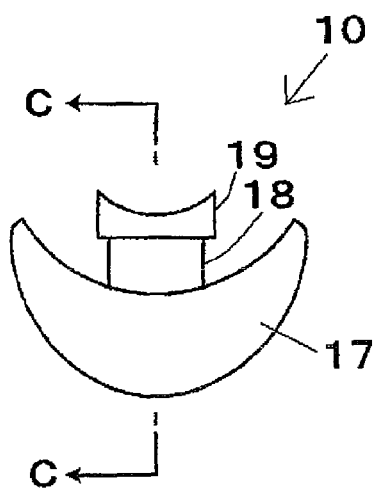
FIG. 6 is a plan view of the bulge of the base material for forming a valved artificial blood vessel.
Figure 7:
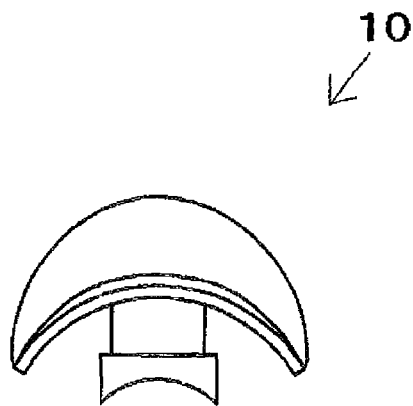
FIG. 7 is a bottom view of the bulge of the base material for forming a valved artificial blood vessel.
Figure 8:
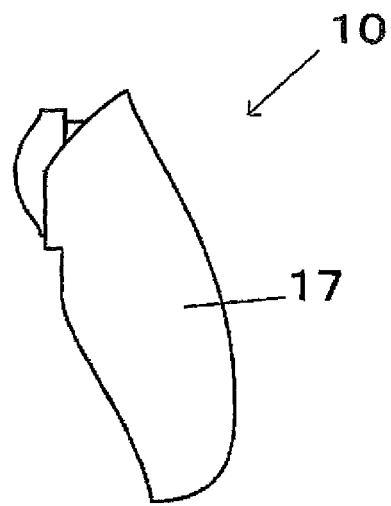
FIG. 8 is a left side view of the bulge of the base material for forming a valved artificial blood vessel.
Figure 9:
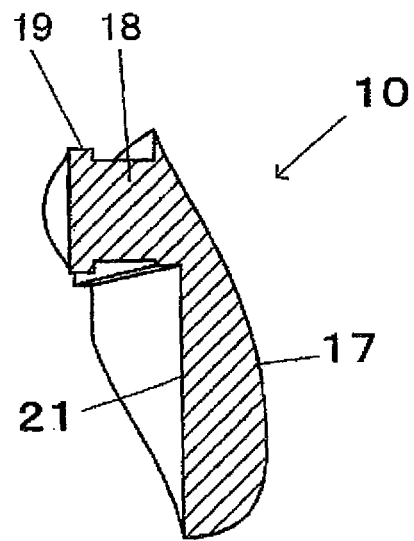
FIG. 9 is a C-C sectional view of the bulge of the base material for forming a valved artificial blood vessel.

As shown in FIG. 3, the bulge body 17 has a curved surface expanding laterally of the first column 5 and the second column 7, and the curved outer peripheral surface is an ampulla forming surface 20 that forms a luminal surface of the ampulla 8. As shown in FIGS. 4 and 5, the bulge body 17 has an upstream edge curved into a U shape. As shown in FIG. 3, three bulge bodies 17 are continuously provided in the circumferential direction. A region 17a of the bulge body 17 on an upper side (downstream in the blood flow direction) of a lower edge (upstream edge) of the engagement section 18 can come into tight contact with the first column 5 and the second column 7. With this structure, a gap between the first column 5 and the second column 7 can be covered to prevent extra penetration of the tissue 2 into the gap.

Figure 12:
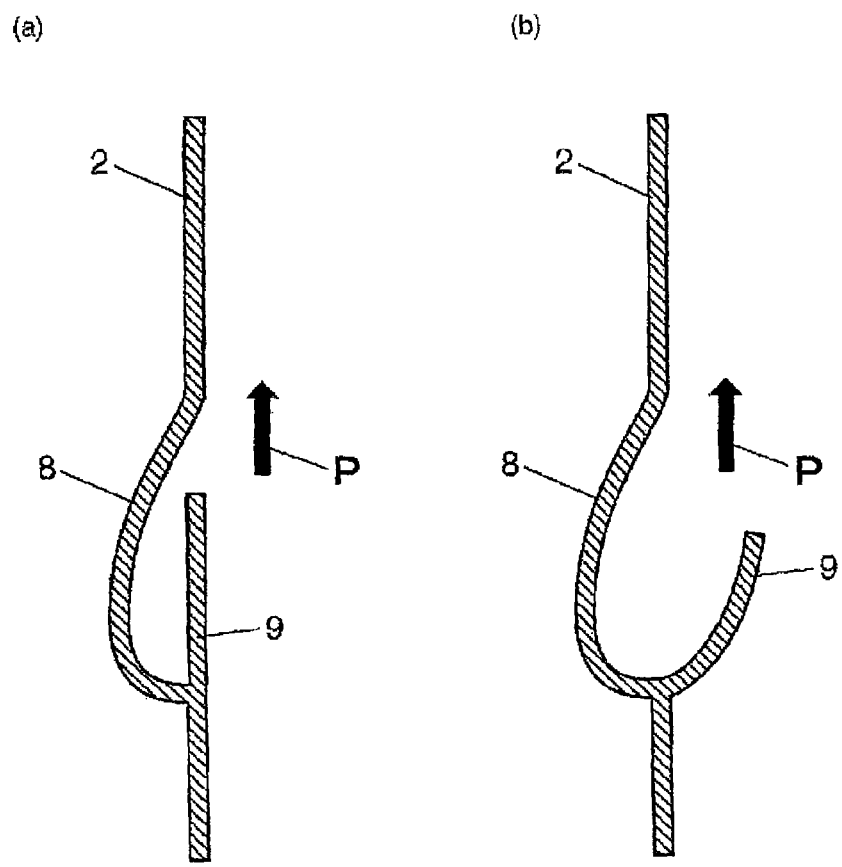
FIG. 12 is an end view showing essential parts of the valved artificial blood vessel.

As shown in FIGS. 2, 5, 9 and 11, the upper region 17a of the bulge body 17 is in tight contact with the first column 5 and the second column 7, but the lower region (upstream side) thereof is stepped so as to be thin. A gap provided between the stepped region 21 and the first column 5 is a leaflet forming section 22. As shown in FIGS. 12(a) and 12(b), the tissue 2 formed in the leaflet forming section 22 can reciprocate radially outward and inward to function as a leaflet 9.

As shown in FIG. 5, a downstream edge 21a of the stepped region 21 forms a downstream edge (tip shape) of the leaflet 9. A downstream edge 21a of the stepped region 21 is tapered toward the downstream of the leaflet, and thus the tip of the leaflet 9 has a tapered square shape. The leaflet forming section 22 (that is, shapes of an inner surface of the bulge body 17 and a corresponding surface of the first column 5) is formed arcuately. This facilitates reciprocation of the leaflet 9 radially outward and inward.

A radial thickness of the leaflet forming section 22 is preferably 0.3 to 1.0 mm, and more preferably 0.3 to 0.8 mm. Even if a leaflet having a thickness within this range is reduced in thickness by a blood flow after transplanted into the body and before stabilized, the leaflet is finally stabilized with a thickness of about 0.2 mm that is substantially the same thickness as a leaflet in a living body, thereby maintaining the function of the valve.

The engagement means 11 includes the recesses 15a and 15b formed in the axial end surfaces of the first column 5 and the second column 7 and axially recessed, and the engagement section 18 of the bulge 10. As shown in FIG. 10, the engagement section 18 is housed in the overlapping region of the recess 15a in the first column 5 and the recess 15b in the second column 7, and axially vertically held between the first column 5 and the second column 7 for engagement to cause the bulge 10 to removably engage the first column 5 and the second column 7. The configuration of the engagement means 11 is not limited to the above as long as the engagement means 11 prevents radial, circumferential, and axial displacement of the bulge 10 with respect to the first column 5 and the second column 7.

The securing means 12 includes the through hole 13 formed to axially pass through the centers of the first column 5 and the second column 7, and a through shaft 24 that is inserted through the through hole 13 to integrally secure the engagement section 18 of the bulge 10, the first column 5, and the second column 7.

The through shaft 24 is made of acrylic resin, and as shown in FIGS. 2 and 10, includes a cylindrical shaft section 25 formed complementary to the through hole 13 in the first column 5 and the second column 7, a disk-shaped shaft base 26 on which the shaft section 25 stands, and a locking section 27 that locks securing of the through shaft 24. An outer diameter of the shaft base 26 is the same as the outer diameter of the first column 5 and the second column 7, and an outer peripheral surface of the shaft base 26 forms a part of the luminal surface of the valved artificial blood vessel 3. The locking section 27 includes a locking hole 28 formed in a tip of the shaft section 25, and an insert 29 that can pass through the locking hole 28. After the shaft section 25 is passed through the through hole 13, an insert 29 is inserted into the locking hole 28 at the tip thereof, and then the insert 29 and the shaft base 26 can hold and secure the first column 5, the second column 7, and the bulge 10 therebetween. As such, the securing means 12 completely secures the first column 5, the second column 7, and the bulge 10, thereby preventing the tissue 2 from being formed on mating surfaces thereof or in the through hole 13.

Next, a method for producing the valved artificial blood vessel 3 using the base material for forming a valved artificial blood vessel 1 as described above will be described. The producing method includes a "placement step" of placing the base material in an environment with a body tissue material, a "taking-out step" of taking out the base material for forming a valved artificial blood vessel 1 covered with the tissue 2 from the environment, and a "separation step" of taking out the base material for forming a valved artificial blood vessel 1 from the tissue 2.

<Placement Step>

First, the base material for forming a valved artificial blood vessel 1 is placed in an environment with living body tissue such as in an animal living body or in an artificial environment such as in a solution in which a body tissue material is suspended outside an animal living body. As a body tissue material, a material derived from mammalian, birds, fish, and other animals, or an artificial material may be used.

To place the base material for forming a valved artificial blood vessel 1 in the animal living body, for example, the base material 1 is embedded by incision into an abdominal cavity having a capacity that receives the base material for forming a valved artificial blood vessel 11, or under the skin of four limbs, shoulder, back, abdomen, or the like, and a wound is then stitched up. For the transplant recipient, any of autologous transplantation, allograft transplantation, and heterotopic transplantation may be used, but autologous transplantation or allograft transplantation is preferable to prevent rejection. For the heterotopic transplantation, elimination of immunogen such as known decellularization is preferably performed to avoid rejection.

When the base material for forming a valved artificial blood vessel 1 is placed in the environment with a body tissue material, various cultivation conditions may be adjusted to perform cell culture in a clean environment according to a known method.

<Taking-Out Step>

After the placement step for a predetermined period, the taking-out step of taking out the base material for forming a valved artificial blood vessel 1 from the environment with a body tissue material is performed. In the base material for forming a valved artificial blood vessel 1 taken out from the environment with a body tissue material, the tissue 2 entirely covered with a film of body tissue is composed of fibroblasts and extracellular matrix such as collagen, and the tissue 2 adheres to the outer peripheral surface of the base material for forming a valved artificial blood vessel 1, but does not penetrate the base material 1.

<Separation Step>

Then, in the separation step, body tissue on one side is removed, and the insert 29 is drawn from the locking hole 28 to release the lock by the locking section 27. Then, body tissue on the other side is removed, and then the shaft section 25 is drawn from the through shaft 24 of the first column 5 and the second column 7 with the shaft base 26. The first column 5 and the second column 7 are axially vertically disassembled from the bulge 10, and each drawn out from upper and lower ends of the lumen of the tissue 2.

Then, the three bulges 10 are drawn out. The bulges 10 are housed in a pocket between the leaflet forming section 22 and the ampulla 8. The bulge 10 is drawn downstream, thereby producing the valved artificial blood vessel 3 composed of the body tissue. The inner surface of the released tissue 2 is in contact with the surface of the base material 1 and is flat.

Figure 13:
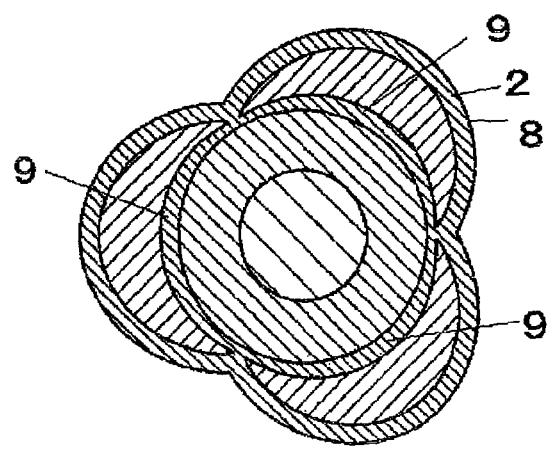
FIG. 13 is a D-D sectional view of FIG. 11.
Figure 14:
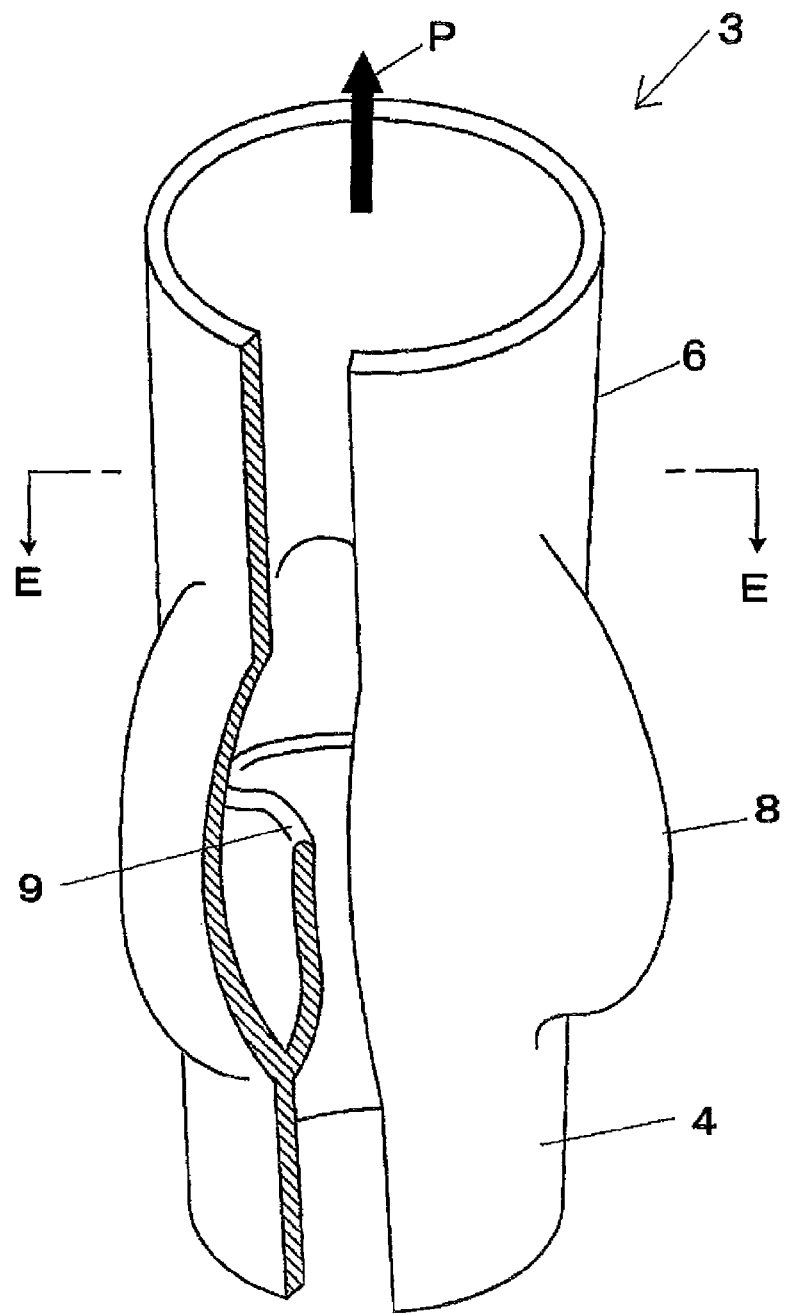
FIG. 14 is a partially cut perspective view of the valved artificial blood vessel.
Figure 15:
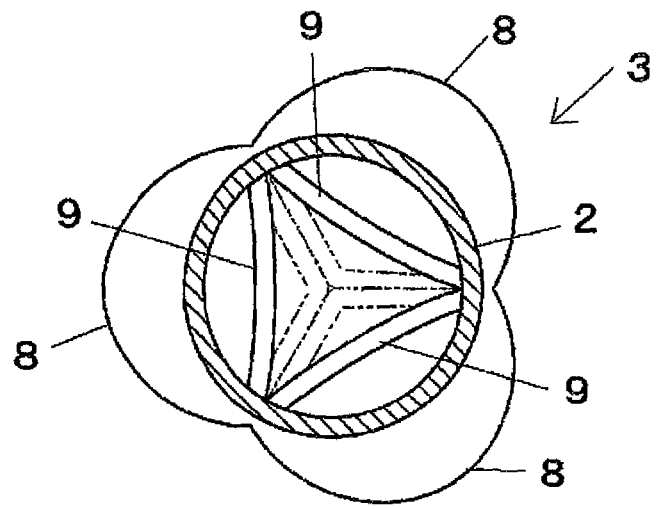
FIG. 15 is an E-E sectional view of FIG. 14.

As shown in FIGS. 13 to 15, in the valved artificial blood vessel 3, the ampulla forming surface 20 on the outer peripheral surface of the bulge 10 forms the ampulla 8 expanding radially outward like a bump. In the ampulla 8, a pocket-like structure is formed in an upstream region, and thus the pocket piece forms the leaflet 9. A state where three leaflets 9 expand and downstream (open side) ends thereof are moved close to each other is a closed state of the valve (region shown by dash-double-dot lines in FIG. 15), and a state where the three leaflets 9 contract and the downstream ends are moved away from each other and close to a wall surface of the ampulla 8 is a fully opened state of the valve (region shown by solid lines in FIG. 15).

As described above, the base material for forming an artificial blood vessel 1 can be easily separated from the tissue 2 in such a manner that the first column 5 and the second column 7 are vertically disassembled from the bulges 10 and taken out from the lumen of the tissue 2, and the plurality of bulges 10 are taken out from the lumens. The base material can be disassembled and taken out, thereby preventing damaging the tissue 2. The formed valved artificial blood vessel 3 can form one completed leaflet 9 in the leaflet forming section 22, and thus the leaflet 9 can be completed without cutting.

Second Embodiment

Figure 16:
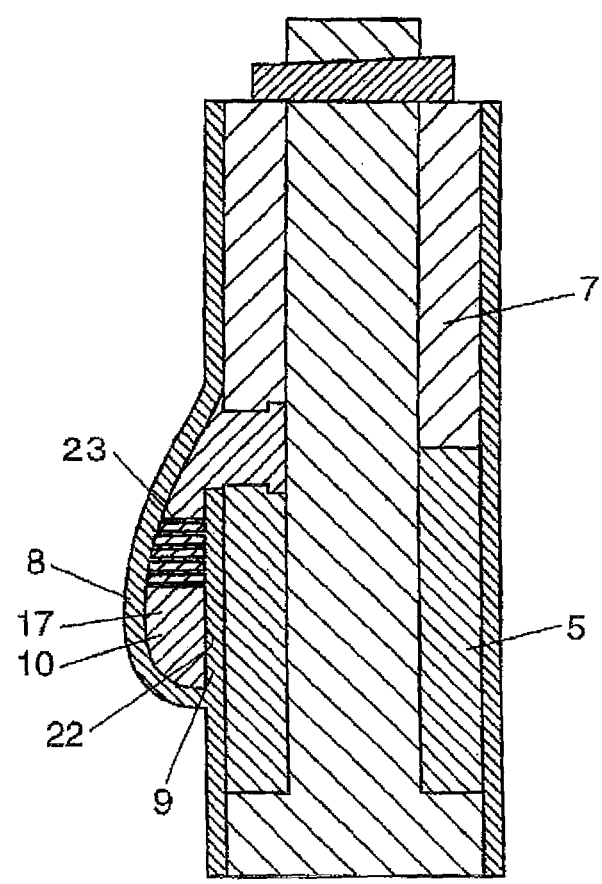
FIG. 16 is a vertical sectional view of a base material for forming a valved artificial blood vessel according to a second embodiment.

In this embodiment, as shown in FIG. 16, a penetration hole 23 radially passing through a bulge body 17 is formed to form a thick leaflet 9 in a shorter period. Since the penetration hole 23 provides communication between a radially outer surface of the bulge body 17 and a leaflet forming section 22, tissue 2 penetrates a gap 22 between a lower edge (upstream edge) of the bulge body 17 and a first column 5, and also the leaflet forming section 22 through the penetration hole 23.

One penetration hole 23 may be provided, but a plurality of penetration holes 23 are preferably provided to facilitate penetration of the tissue 2 into the leaflet forming section 22. In the case where the penetration hole 23 is provided, the tissue 2 needs to be cut on at least one side of the penetration hole 23 when a bulge 10 is drawn from the tissue 2 formed on a surface of a base material 1. A diameter of the penetration hole 23 is preferably 0.5 to 1.0 mm. This is because a diameter of less than 0.5 mm prevents penetration of cells, and a diameter of more than 1.0 mm prevents cutting of the tissue 2.

Third Embodiment

Figure 17:
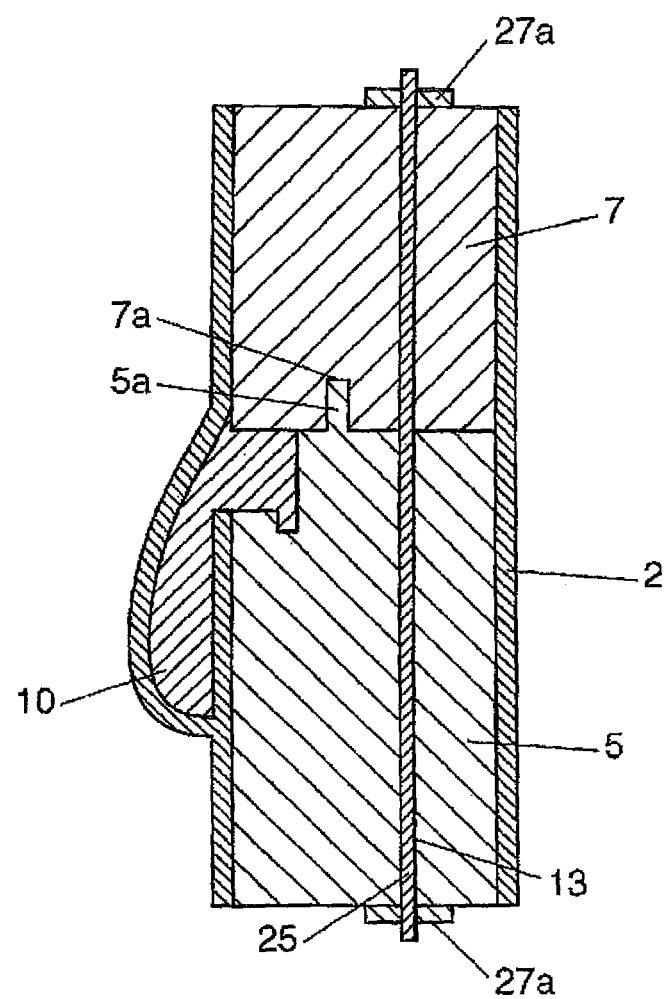
FIG. 17 is a vertical sectional view of a base material for forming a valved artificial blood vessel according to a third embodiment.

In this embodiment, as shown in FIG. 17, a through hole 13 is formed in a position outside centers of a first column 5 and a second column 7 instead of being formed in the centers of the first column 5 and the second column 7.

Also, a protruding portion 5a protrudes from the first column 5 (or second column 7), and a depression 7a is provided in the second column 7 (or first column 5). The protruding portion 5a is inserted and fitted into the depression 7a to prevent displacement in a direction perpendicular to axes of the first column 5 and the second column 7.

A through shaft 24 of securing means 12 may include a shaft section 25, and locking sections that secure opposite ends of the shaft section 25. The locking sections include male threads formed on the opposite ends of the shaft section 25, and nuts 27a. After the shaft section 25 is inserted through the through hole 13 in the first column 5 and the second column 7, the shaft section 25 is fastened by the nuts 27a from the opposite ends of the shaft section 25, and thus the first column 5, the bulge 10, and the second column 7 can be integrally secured between the two nuts 27a.

Fourth Embodiment

Figure 18:
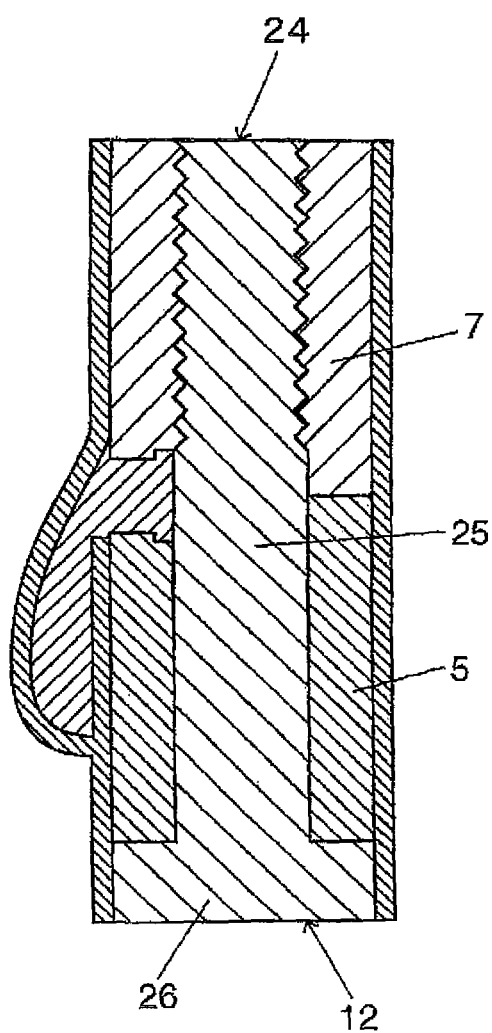
FIG. 18 is a vertical sectional view of a base material for forming a valved artificial blood vessel according to a fourth embodiment.

In this embodiment, as shown in FIG. 18, securing means 12 includes a male thread provided on an outer periphery of a shaft section 25 of a through shaft 24, and a female thread formed on a peripheral surface of a through hole 13 in a first column 5 and/or a second column 7. This configuration eliminates the need for a locking section 27, and can reduce the number of components. Specifically, the female thread is partially or entirely provided on the peripheral surface of the through hole 13 in the second column 7, the shaft section 25 is inserted into the through hole 13 from the side of the first column 5 without the female thread, and fastened by the threads in the through hole 13 in the second column 7. Thus, the shaft base 26 and the second column 7 can hold and secure the first column 5 and the bulge 10 therebetween. The female thread may be provided on the first column 5 rather than on the second column 7, or female threads may be provided on both the first column 5 and the second column 7.

Fifth Embodiment

Figure 19:
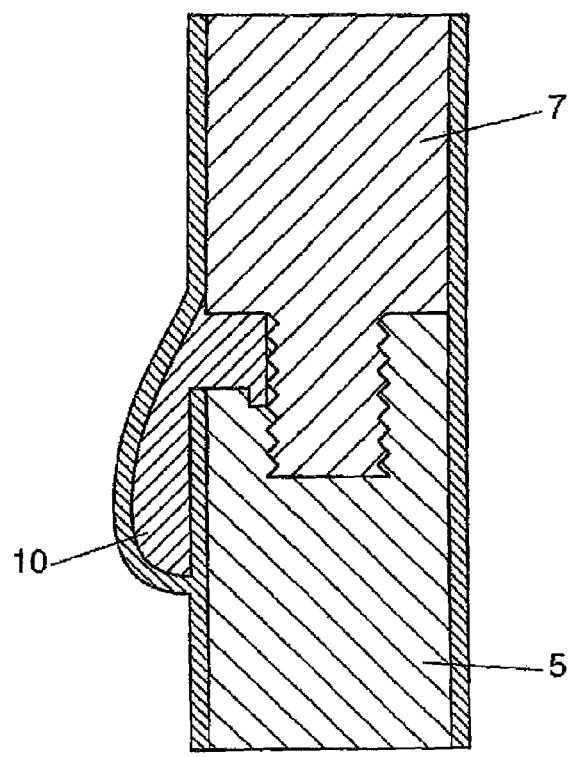
FIG. 19 is a vertical sectional view of a base material for forming a valved artificial blood vessel according to a fifth embodiment.

In this embodiment, as shown in FIG. 19, securing means 12 includes a male thread formed on a second column 7, and a female thread formed on a first column 5 so as to be screwed onto the male thread. The male thread on the second column 7 is screwed onto the female thread on the first column 5, thereby integrally securing the first column 5, the second column 7, and the bulge 10. The male thread may be provided on the first column 5, and the female thread may be provided on the second column 7.

Sixth Embodiment

Figure 20:
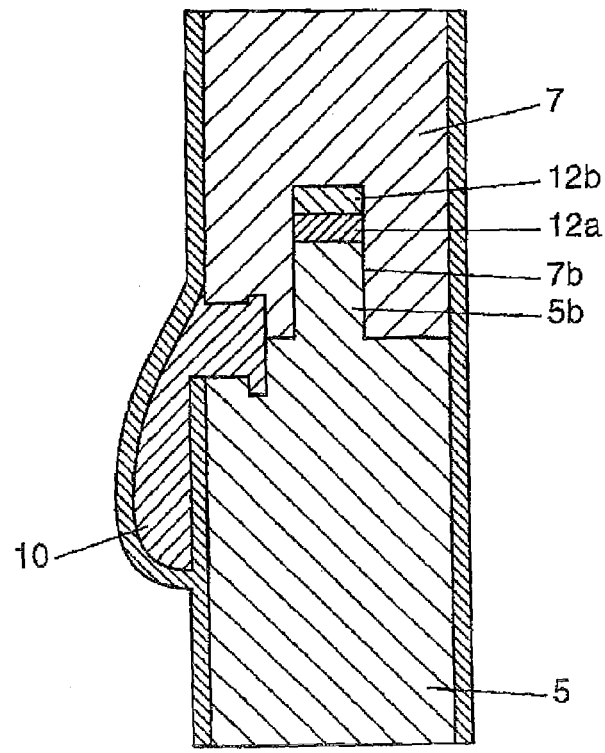
FIG. 20 is a vertical sectional view of a base material for forming a valved artificial blood vessel according to a sixth embodiment.

In this embodiment, as shown in FIG. 20, a magnetic material 12a is provided on a first column 5 (or second column 7), and a magnetized material 12b is provided on a second column 7 (or first column 5). The magnetic material 12a and the magnetized material 12b are attracted to each other, thereby integrally securing the first column 5, the second column 7, and the bulge 10. The magnetic material 12a and the magnetized material 12b may be provided on end surfaces of the first column 5 and the second column 7 respectively, but if the magnetic material 12a is provided on a tip of a protrusion 5b protruding from the first column 5 (or second column 7), and the magnetized material 12b is provided on a bottom of a fitting recess 7b formed in the second column 7 (or first column 5), the protrusion 5b of the first column 5 may be inserted into the fitting recess 7b in the second column 7 for more fixed securing.

Seventh Embodiment

Figure 21:
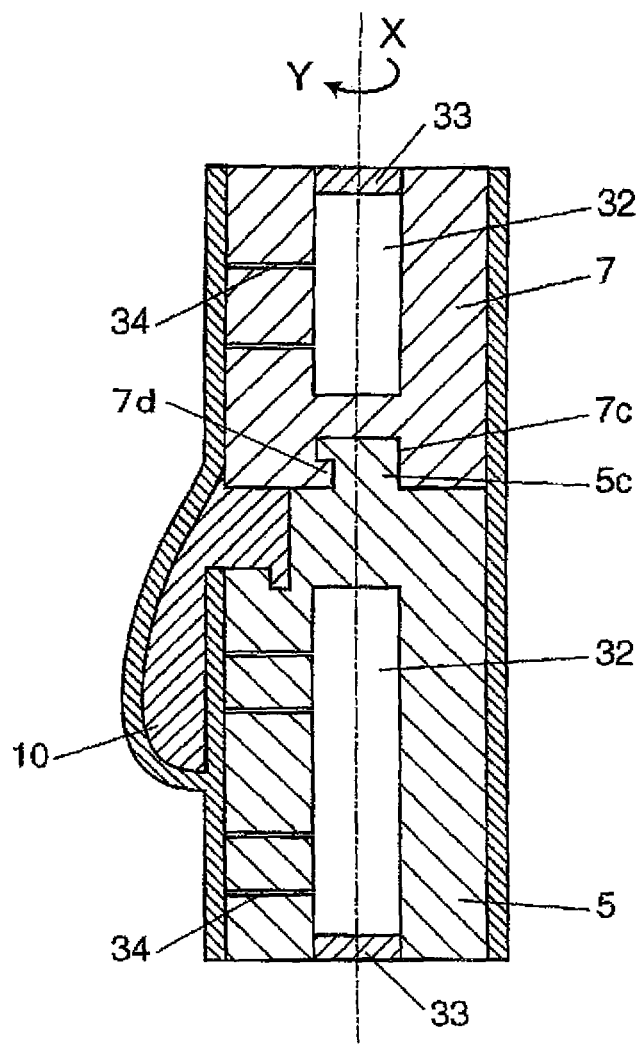
FIG. 21 is a vertical sectional view of a base material for forming a valved artificial blood vessel according to a seventh embodiment.

In this embodiment, as shown in FIG. 21, securing means 12 includes an engagement pawl 5c having a bent tip and placed on a first column 5 (or second column 7), and an engagement hole 7c formed in the second column 7 (first column 5). The engagement hole 7c has a stop structure 7d, the engagement pawl 5c of the first column 5 is inserted into the engagement hole 7c in the second column 7, then the first column 5 is rotated 90 degrees from X to Y around the axis, and thus the bent region at the tip of the engagement pawl 5c is caught by the stop structure 7d of the engagement hole 7c. With this structure, the first column 5 can removably engage the second column 7. The engagement hole may be provided in the first column 5, and the engagement pawl may be provided on the second column 7.

Also, a void section 32 for housing a drug provided in the first column 5 and the second column 7, a lid 33 for opening/closing an opening of the void section 32, and a leaching path 34 extending radially outward from the void section 32 and opening in the outer surfaces of the columns 5 and 7. After a drug is placed through the opening of the void section 32, the base material for forming a valved artificial blood vessel 1 is placed in an environment with a body tissue material with the lid 33 being closed, and the drug in the void section 32 can be leached to the outside of the base material 1 through the leaching path 34. A diameter of the leaching path 34 is preferably 0.5 mm or less. The diameter of 0.5 mm or less can prevent penetration of cells into the leaching path 34.

Drugs may include a drug for promoting formation of the tissue 2, for example, an endothelial cell growth promoter (such as angiogenic factors HFG, VEGF or bFGF), but not limited to them.

Eighth Embodiment

Figure 22:
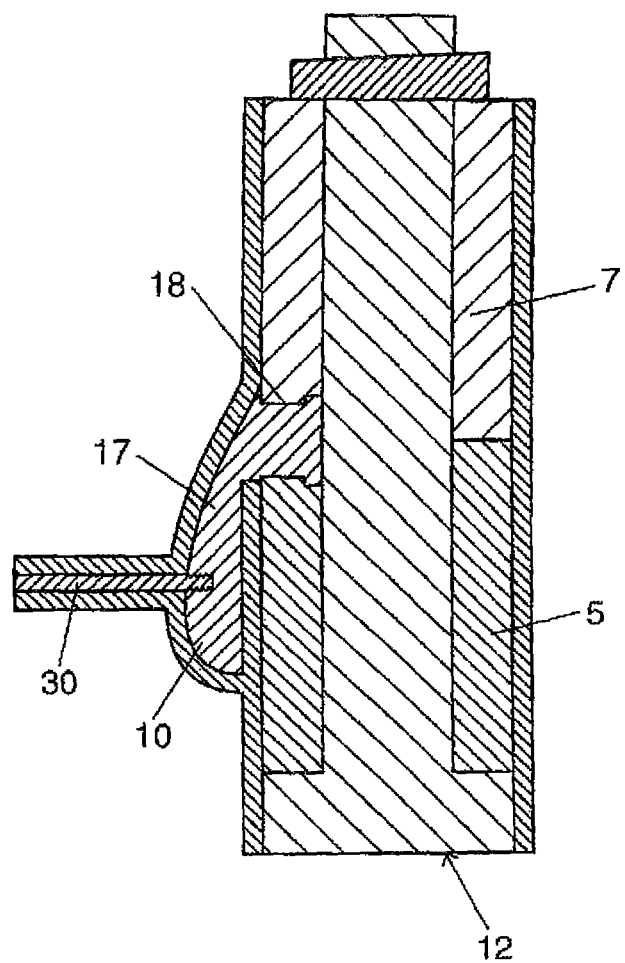
FIG. 22 is a vertical sectional view of a base material for forming a valved artificial blood vessel according to an eighth embodiment.

In this embodiment, as shown in FIG. 22, a third column 30 connected to an outer surface of one or more bulge bodies 17 is provided. The third column 30 is preferably removably provided on the outer surface of the bulge body 17. For example, a female thread is formed in a hole formed in the bulge body 17, and a male thread is formed on a tip of the third column 30, and thus the third column 30 may be removably provided by fastening by the threads. The third column 30 is provided on the outer surface of the bulge body 17, and thus the outer peripheral surface of the third column 30 is a forming surface of a blood vessel lumen branching off from an ampulla 8.

Ninth Embodiment

Figure 23:
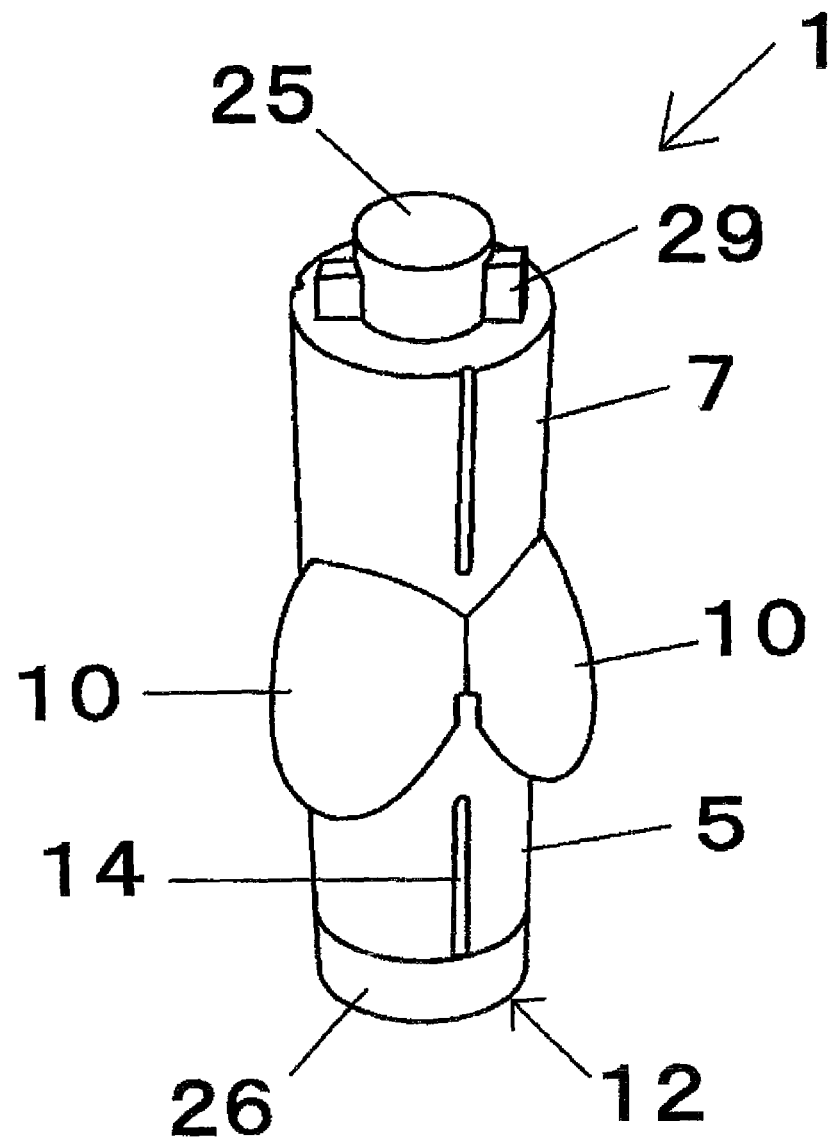
FIG. 23 is a perspective view of a base material for forming a valved artificial blood vessel according to a ninth embodiment.

In this embodiment, as shown in FIG. 23, recesses 15a and 15b are provided only on a second column 7 rather than on both a first column 5 and the second column 7 to displace engagement means 11 toward the first column 5. A bulge body 17 circumferentially covers a boundary between the first column 5 and the second column 7 to cover an entire gap between the first column 5 and the second column 7. A leaflet forming section 22 is formed between the first column 5 and the second column 7, and the bulge body 17. The recesses 15a and 15b may be provided only on the first column 5.

Tenth Embodiment

Figure 24:
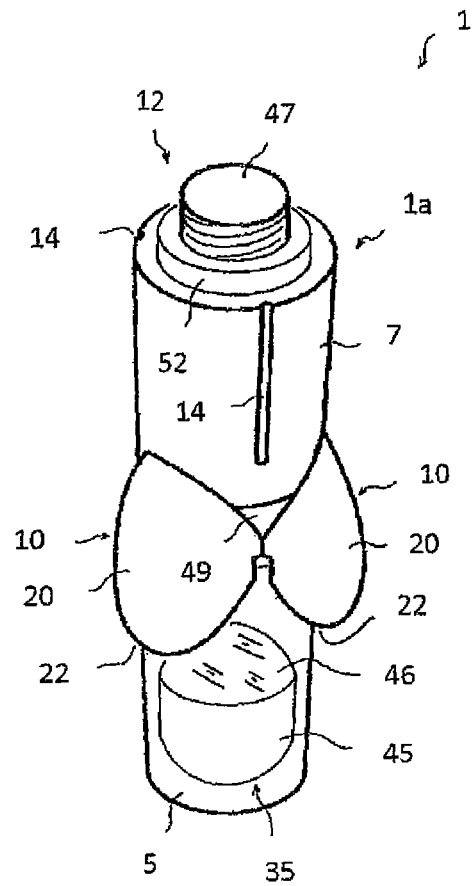
FIG. 24 is a perspective view of a base material for forming a valved artificial blood vessel according to a tenth embodiment.
Figure 25:
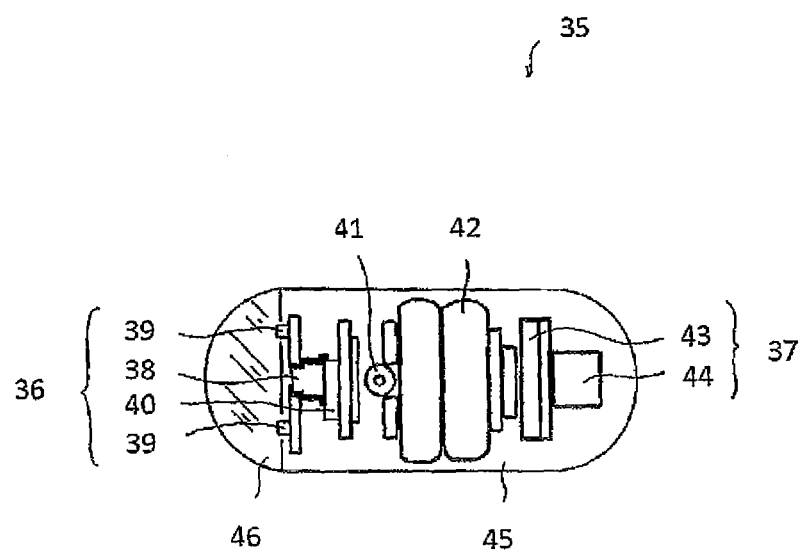
FIG. 25 is a schematic diagram of a body tissue formation observation apparatus.
Figure 26:
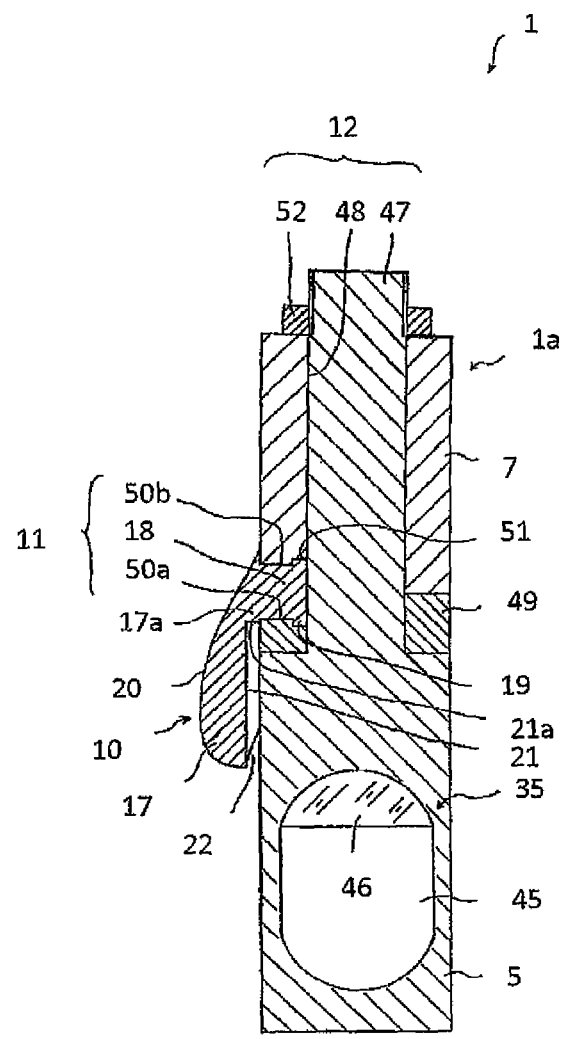
FIG. 26 is a vertical sectional view of the base material for forming a valved artificial blood vessel.

In this embodiment, as shown in FIGS. 24 to 26, the base material for forming a valved artificial blood vessel 1 includes a body tissue formation observation apparatus 35 that transmits an image of tissue 2 formed around a base material body 1a to the outside of the environment.

The base material body 1a has substantially the same configuration as the base material for forming a valved artificial blood vessel 1 of the first embodiment, and includes a first column 5 that forms an upstream tubular section 4 of an artificial blood vessel 3, a second column 7 that forms a downstream tubular section 6 of an artificial blood vessel 3, a plurality of bulges 10 for forming an ampulla 8 and a leaflet 9, engagement means 11 that causes a bulge 10 to removably engage the first column 5 and the second column 7, and securing means 12 that integrally secures the first column 5, the second column 7, and the bulge 10.

The body tissue formation observation apparatus 35 includes photographing means 36 that photographs the tissue 2 formed around the base material body 1a, and transmission means 37 that transmits an image such as a moving image or a picture photographed by the photographing means 36 to the outside of the environment, and is embedded in an end of the first column 5 made of, for example, see-through translucent silicone resin. Thus, the tissue 2 formed to penetrate a leaflet forming section 22 can be photographed and checked, and it can be determined that the tissue 2 is formed on an ampulla forming surface 20 on which the tissue 2 is more easily formed.

As shown in FIG. 25, the body tissue formation observation apparatus 35 used as, for example, a known capsule endoscope may be used, and can be intermittently used by magnetic on/off operation from outside of the environment. This reduces, for example, battery drain and allows a long-hour observation until sufficient formation of the body tissue 2.

The body tissue formation observation apparatus 35 includes photographing means 36 having a lens 38, an LED 39, and a high resolution CCD 40, for photographing the tissue 2, a magnetic switch 41 that can be operated from outside, a small battery 42 that supplies electricity, and transmission means 37 having a radio transmitter 43 and a radio antenna 44, all of which are housed in a container 45. A window 46 made of a transparent material is provided in a front of the housing container 45 so that the photographing means 36 applies, for example, a visible light to the tissue 2 using the LED 39 and photographs the tissue 2 from the inside of the housing container 45. The image photographed by the photographing means 36 is converted into a signal and transmitted to the outside by the transmission means 37, and the signal is received outside for outside image observation.

The first column 5 is a cylinder made of silicone resin, the second column 7 is a cylinder made of acrylic resin, and both have an outer diameter of 20 mm and an entire length of about 30 mm. A through shaft 47 having a diameter of about 10 mm is formed in a center of a downstream end surface of the first column 5, and passes through a through hole 48 having a diameter of about 10 mm formed in a center of the second column 7.

An engagement ring 49 for engagement of the bulge 10 is externally fitted to a proximal end of the through shaft 47 of the first column 5, and a plurality of axially recessed recesses 50a and 50b are formed in mating end surfaces of the engagement ring 49 and the second column 7. Three recesses 50a and three recesses 50b are formed to match the number of leaflets 9, and formed in corresponding positions between the first column 5 and the second column 7. The recesses 50a and 50b each have an engagement groove 51 with a radially inward side being wide.

The bulge 10 has the same configuration as in the first embodiment, includes a bulge body 17, and an engagement section 18 overhanging radially inward from the bulge body 17. The engagement section 18 engages an overlapping region of the recess 50a in the engagement ring 49 and the recess 50b in the second column 7.

The securing means 12 includes the through shaft 47 on the first column 5, the through hole 48 in the second column 7, and a nut 52 that is screwed on a tip of the through shaft 47 passing through the through hole 48 to integrally secure the engagement section 18 of the bulge 10, the first column 5, the engagement ring 49, and the second column 7.

Next, a method for producing the valved artificial blood vessel 3 using the base material for forming a valved artificial blood vessel 1 as described above will be described.

This production method is substantially the same as the method in the first embodiment, and in the placement step, film-like tissue 2 is formed around the base material for forming a valved artificial blood vessel 1, and a formation state of the tissue 2 is observed by the body tissue formation observation apparatus 35, and it is determined whether the process moves to the "taking-out step" or not. At this time, the body tissue formation observation apparatus 35 is operated on/off from the outside of the environment to intermittently observe the formation state of the body tissue 2.

Figure 27:
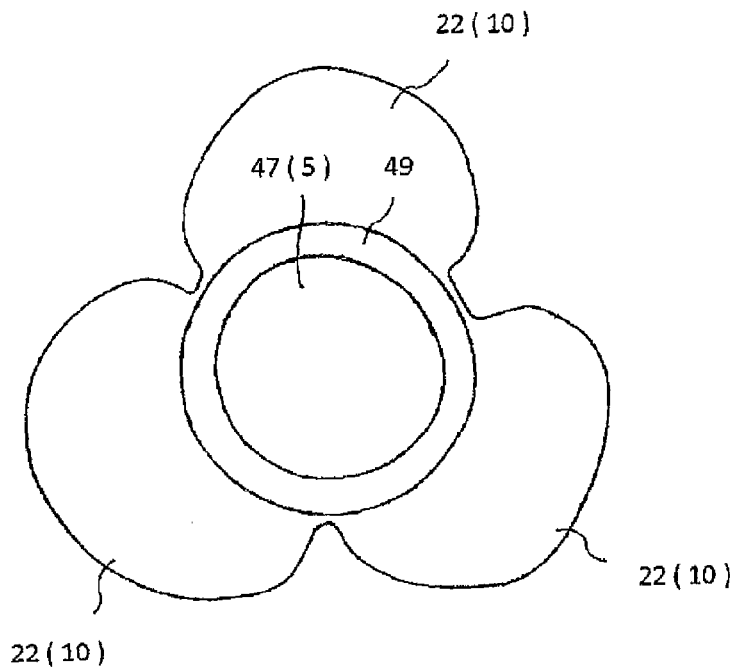
FIG. 27 is a view showing an image of the base material for forming a valved artificial blood vessel transmitted by a body tissue formation observation apparatus.
Figure 28:
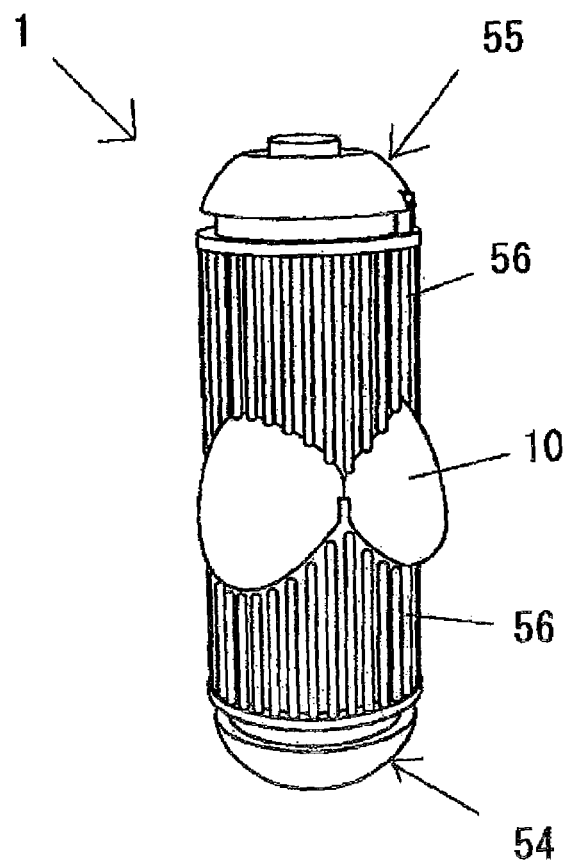
FIG. 28 is a perspective view of a base material for forming a valved artificial blood vessel according to an eleventh embodiment.

As shown in FIG. 27, the image photographed by the body tissue formation observation apparatus 35 shows an inner surface side (leaflet forming section 22) of the bulge 10 seen through the see-through material from the inside of the first column 5. Initially when the base material for forming a valved artificial blood vessel 1 is placed, there is a void in the leaflet forming section 22. Then, the tissue 2 gradually penetrates the void in the leaflet forming section 22 to eventually form the leaflet 9 in the leaflet forming section 22. Further, in a state where the tissue 2 sufficiently penetrates into the leaflet forming section 22 to form the leaflet 9, the tissue 2 is also formed on the ampulla forming surface 20 on which the tissue 2 is easily formed.

Eleventh Embodiment

Figure 29:
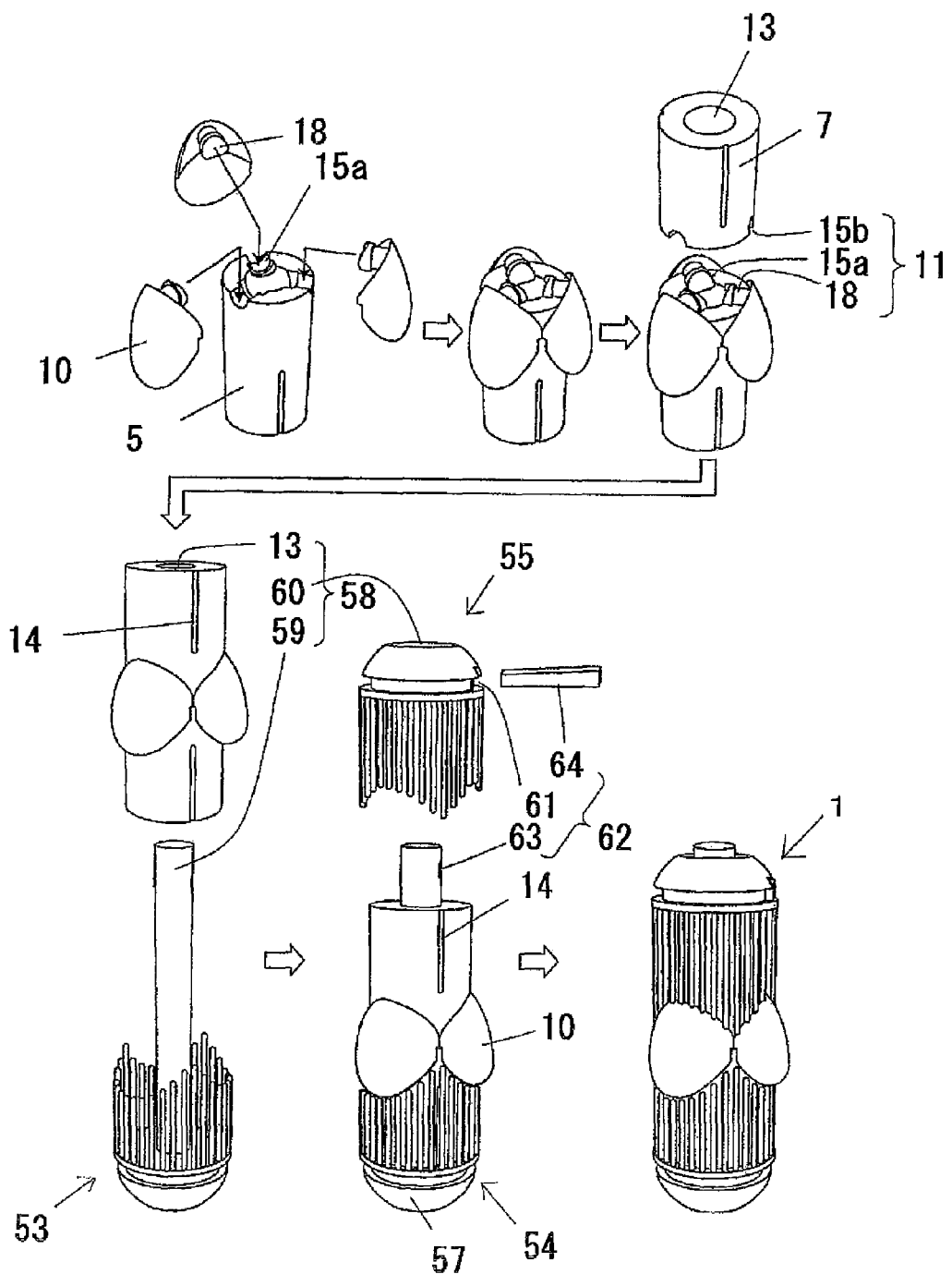
FIG. 29 is a view showing an assembling process of the base material for forming a valved artificial blood vessel.
Figure 30:
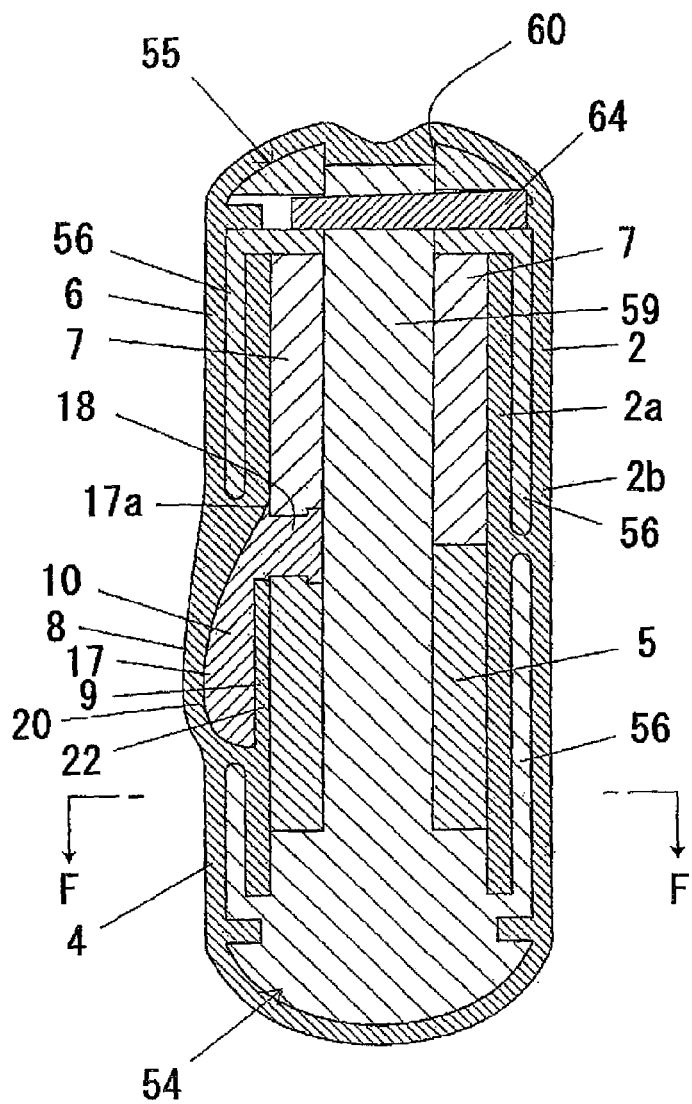
FIG. 30 is a vertical sectional view of the base material for forming a valved artificial blood vessel being covered with tissue.
Figure 31:
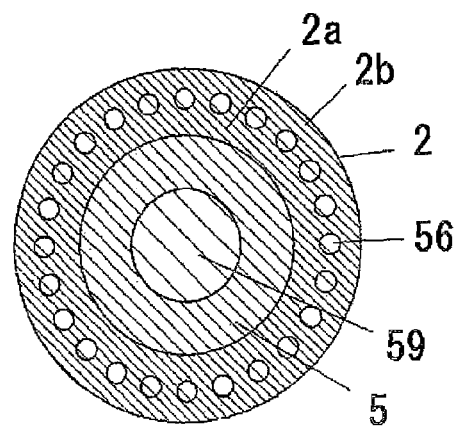
FIG. 31 is an F-F sectional view of FIG.
Figure 32:
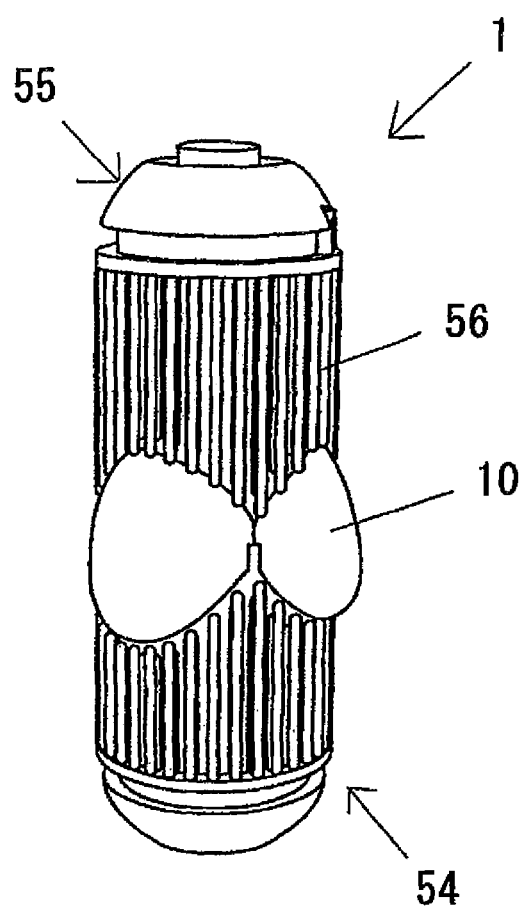
FIG. 32 is a perspective view of a base material for forming a valved artificial blood vessel according to a twelfth embodiment.
Figure 33:
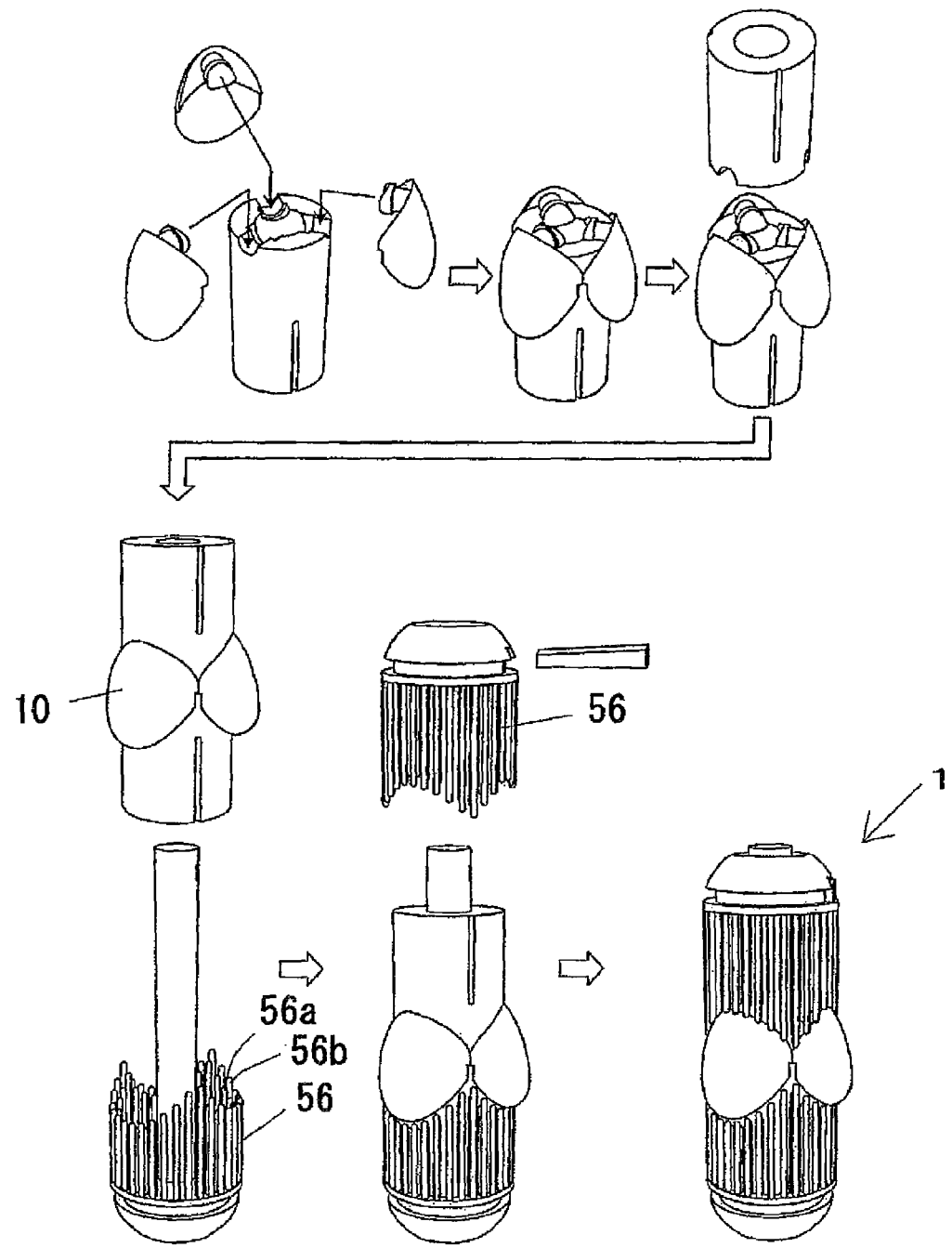
FIG. 33 is a view showing an assembling process of the base material for forming a valved artificial blood vessel.
Figure 34:
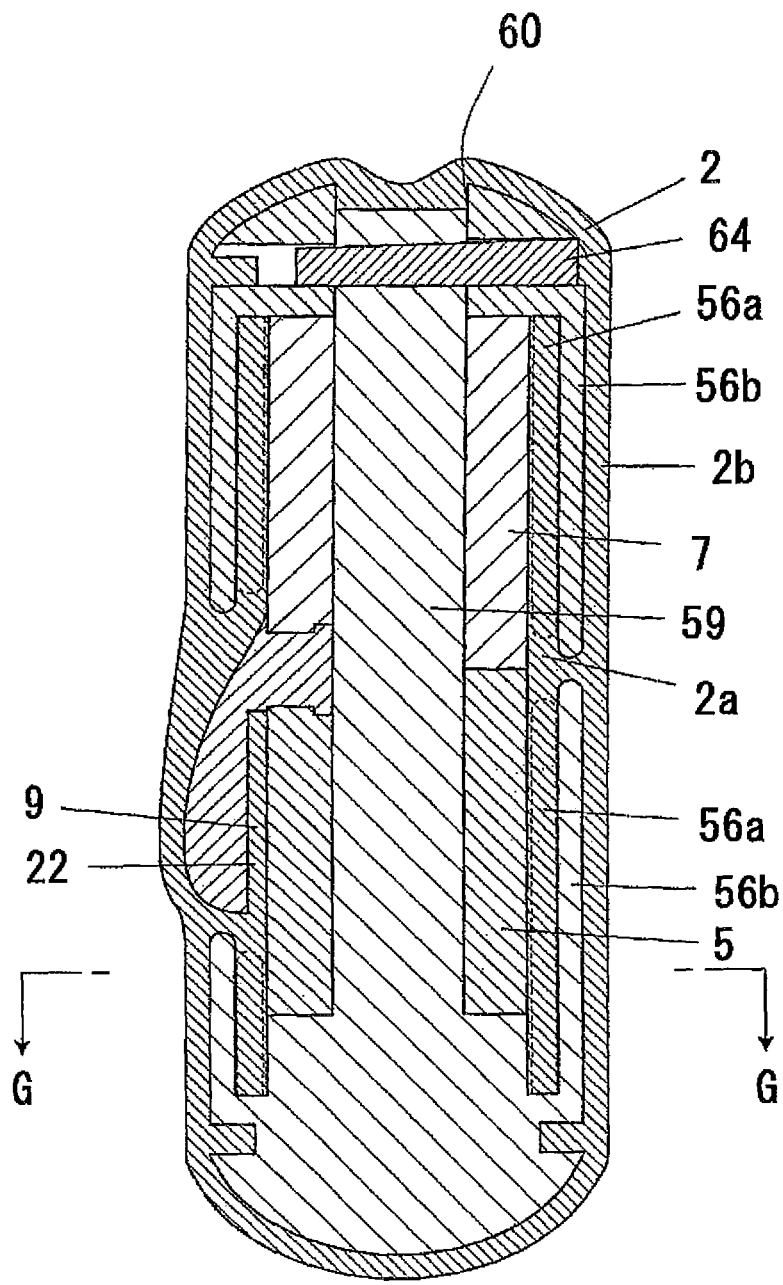
FIG. 34 is a vertical sectional view of the base material for forming a valved artificial blood vessel being covered with tissue.
Figure 35:
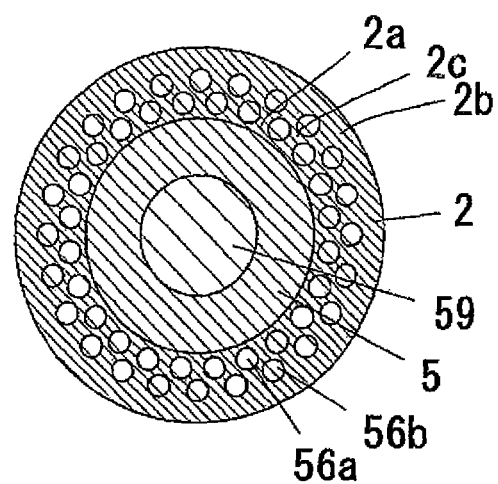
FIG. 35 is a G-G sectional view of FIG. 34.
Figure 36:
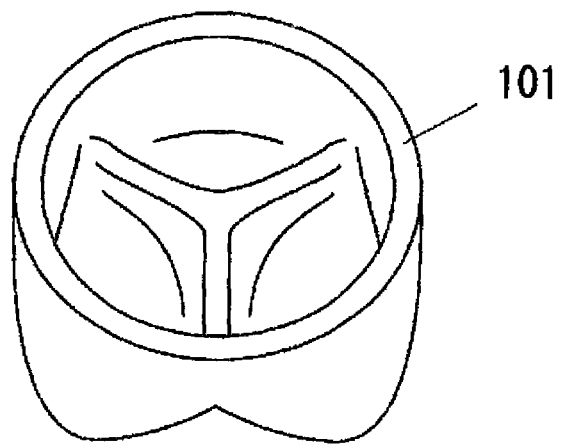
FIG. 36 is a perspective view showing a conventional scaffold.

As shown in FIGS. 29 to 31, this embodiment has substantially the same configuration as the first embodiment, and an auxiliary structure 53 is spaced radially outward from outer surfaces of the first column 5 and the second column 7.

As shown in FIG. 29, the auxiliary structure 53 includes a first auxiliary structure 54 and a second auxiliary structure 55, and auxiliary structures 53 are removably provided to face each other on outer end sides of the first column 5 and the second column 7. Each auxiliary structure 53 is made of silicone resin. Each auxiliary structure 53 includes auxiliary columns 56 arranged around the first column 5 and the second column 7, and a support 57 that supports ends of the auxiliary columns 56, and is removably connected to the first column 5 and the second column 7 by connection means 58.

The support 57 has a substantially cylindrical shape having a larger diameter than the first column 5 and the second column 7. A rod-like through shaft 59 axially stands on an inner wall surface of the support 57 of the first auxiliary structure 54. A support through hole 60 is axially formed in a center of the support 57 of the second auxiliary structure 55. An engagement hole 61 is radially formed in the support 57 of the second auxiliary structure 55, and the engagement hole 61 provides communication between the support through hole 60 and the outside.

The auxiliary column 56 has a rod shape, and one end thereof is secured to the support 57 so as to be spaced radially outward from the outer surfaces of the first column 5 and the second column 7, and extends axially in parallel with the first column 5 and the second column 7. The auxiliary column 56 is spaced, for example, about 0.5 to 1.0 mm from the outer surfaces of the first column 5 and the second column 7, and has a thickness of, for example, 0.5 mm to 2.0 mm, preferably 0.8 mm to 1.2 mm. A plurality of auxiliary columns 56 are provided in a circumferential direction of the first column 5 and the second column 7, tips of the auxiliary columns 56 extend to the edge of the bulge body 17 to cover the outer peripheral surfaces of the first column 5 and the second column 7. The auxiliary columns 56 are spaced from each other, and tissue 2 is introduced through the gaps to fill a space between the first column 5 and the second column 7, and the auxiliary columns 56.

The connection means 58 includes a through shaft 59 of one support 57, the through hole 13 in the first column 5 and the second column 7, and the support through hole 60 in the other support 57, and connects the auxiliary structure 53 and integrally secures the first column 5, the second column 7, and the bulge 10. The auxiliary structure 53 may be axially removably connected to the ends of the first column 5 and the second column 7.

The through shaft 59 is made of acrylic resin, and is formed complementary to the through hole 13 in the first column 5 and the second column 7 and the support through hole 60 in the support 57, and can be locked through the through hole 13 and the support through hole 60 by a locking section 62. The locking section 62 includes a locking hole 63 formed on a tip side of the through shaft 59, an engagement hole 61 in the second column 7, and an insert 64 that can pass through the locking hole 63 and the engagement hole 61.

The through shaft 59 is passed through the through hole 13 and the support through hole 60, and the insert 64 is inserted into the engagement hole 61 and the locking hole 63, and thus the first column 5, the second column 7, and the bulge 10 are held between the insert 64 and the support 57 and integrated, and the auxiliary structure 53 is connected thereto. The first column 5, the second column 7, and the bulge 10 are completely secured, thereby preventing formation of the tissue 2 on mating surfaces thereof or in the through hole 13.

Next, the separation step in the production method of the valved artificial blood vessel 3 will be described. First, the tissue 2 that covers the opposite ends of the base material for forming a valved artificial blood vessel 1 is removed, the insert 64 is drawn from the locking hole 63 and the engagement hole 61, the second auxiliary structure 55 is drawn from the through shaft 59, and the through shaft 59 of the first auxiliary structure 54 is drawn from the first column 5 and the second column 7. At this time, the first auxiliary structure 54 and the second auxiliary structure 55 are axially drawn so as not to break the tissue 2.

Then, the first column 5 and the second column 7 are axially disassembled from the bulge 10, and drawn from the lumen of the tissue 2, and further the three bulges 10 are drawn downstream. Thus, a thick valved artificial blood vessel 3 with inner layer tissue 2a and outer layer tissue 2b inside and outside the auxiliary structure 53 being integrated can be formed.

Twelfth Embodiment

This embodiment has substantially the same configuration as the eleventh embodiment, but as shown in FIGS. 32 to 35, auxiliary columns 56 are provided in two layers radially of a first column 5 and a second column 7, and the auxiliary columns 56 are in two layers of an inner layer 56a and an outer layer 56b. The auxiliary columns 56 may be provided in three or more layers. As such, the auxiliary columns 56 are provided in a plurality of layers, thereby integrating inner layer tissue 2a, outer layer tissue 2b, and middle layer tissue 2c to further increase a thickness of the tissue 2.

REFERENCE SIGNS LIST 1 base material for forming valved artificial blood vessel
2 tissue
3 valved artificial blood vessel
4 upstream tubular section
5 first column
6 downstream tubular section
7 second column
8 ampulla
9 leaflet
10 bulge
11 engagement means
12 securing means
13 through hole
15a, 15b recess
17 bulge body
18 engagement section
20 ampulla forming surface
22 leaflet forming section
23 penetration hole
24 through shaft
30 third column
35 body tissue formation observation apparatus
36 photographing means
37 transmission means
47 through shaft
48 through hole
49 engagement ring
50a, 50b recess
52 nut
2a inner layer tissue
2b outer layer tissue
2c middle layer tissue
53 auxiliary structure
58 connection means
54 first auxiliary structure
55 second auxiliary structure
56 auxiliary column
57 support
59 through shaft
60 support through hole
62 locking section
63 locking hole
64 insert

The invention claimed is:

1. A base material for forming valved lumen shape tissue that is placed in an environment with a body tissue material to form film-like tissue on a surface thereof, and from which the tissue is released to form valved lumen shape tissue, comprising:
   a first column that forms an upstream tubular section of the lumen shape tissue; a second column that forms a downstream tubular section of the lumen shape tissue; a plurality of bulges for forming an ampulla provided between the upstream tubular section and the downstream tubular section and having a lumen shape tissue wall expanding radially outward, and a leaflet that protrudes radially inward in the ampulla and is openable/closable in a flow direction;
   engagement means that causes the bulge to removably engage the first column and/or the second column; and securing means that integrally secures the first column, the second column, and the bulge,
   wherein the engagement means includes a recess that is formed in an axial end surface of one or both of the first column and the second column and is axially recessed, and an engagement section that overhangs radially inward from a body of the bulge to engage the recess, and thus regulates radial, circumferential, and axial displacement of the bulge with respect to the first column and the second column, and
   an outer peripheral surface of the body of the bulge is an ampulla forming surface, and a gap provided between the bulge body and the first column and/or the second column is a leaflet forming section.

2. The base material for forming valved lumen shape tissue according to claim 1, wherein the securing means includes a through hole formed to axially pass through centers of the first column and the second column, and a through shaft that is inserted through the through hole to integrally secure the engagement section of the bulge, the first column, and the second column.

3. The base material for forming valved lumen shape tissue according to claim 2, wherein the securing means includes a male thread provided on an outer periphery of the through shaft, and a female thread formed on a peripheral surface of the through hole in the first column and/or the second column so as to be screwed onto the male thread.

4. The base material for forming valved lumen shape tissue according to claim 1, wherein the securing means includes a male thread formed on one of the first column and the second column, and a female thread formed on the other of the first column and the second column so as to be screwed onto the male thread.

5. The base material for forming valved lumen shape tissue according to claim 1, wherein the securing means includes a magnetic material placed on one of the first column and the second column, and a magnetized material that is placed on the other of the first column and the second column and attracted to the magnetic material.

6. The base material for forming valved lumen shape tissue according to claim 1, wherein the securing means includes an engagement pawl placed on one of the first column and the second column, and an engagement hole formed in the other of the first column and the second column so as to removably engage the engagement pawl.

7. The base material for forming valved lumen shape tissue according to claim 1, wherein the bulge body includes a penetration hole that provides communication between a radially outer side of the bulge body and the leaflet forming section, and causes the tissue to easily penetrate the leaflet forming section.

8. The base material for forming valved lumen shape tissue according to claim 1, further comprising a third column connected to an outer surface of one or more bulge bodies, wherein an outer peripheral surface of the third column is a forming surface of the lumen shape tissue branching off from the ampulla.

9. The base material for forming valved lumen shape tissue according to claim 1, further comprising, at an end of the first column, a body tissue formation observation apparatus including photographing means that photographs the leaflet forming section, and transmission means that transmits an image photographed by the photographing means to the outside of the environment with a body tissue material.

10. The base material for forming valved lumen shape tissue according to claim 9, wherein a section of the first column housing at least the photographing means of the body tissue formation observation apparatus is made of a see-through material.

11. The base material for forming valved lumen shape tissue according to claim 9, wherein the body tissue formation observation apparatus can be intermittently used by on/off operation from the outside of the environment with a body tissue material.

12. The base material for forming valved lumen shape tissue according to claim 1, wherein an auxiliary structure is spaced radially outward from the outer surfaces of the first column and the second column.

13. The base material for forming valved lumen shape tissue according to claim 12, wherein the auxiliary structure includes auxiliary columns arranged around the first column and the second column, and the auxiliary columns are arranged at the same distance from and inclined to, or in parallel with the axes of the first column and the second column so that the auxiliary columns can be drawn axially with respect to the first column and the second column.

14. The base material for forming valved lumen shape tissue according to claim 12, wherein the auxiliary structure is removably provided on the first column and/or the second column.

15. The base material for forming valved lumen shape tissue according to claim 1, wherein a valved artificial blood vessel is formed as the valved lumen shape tissue.

16. A method for producing valved lumen shape tissue comprising:
a placement step of placing a base material for forming valved lumen shape tissue according to claim 1 in an environment with a body tissue material;
a taking-out step of taking out the base material for forming valved lumen shape tissue covered with tissue from the environment; and
a separation step of taking out the base material for forming valved lumen shape tissue from the tissue,
wherein in the separation step, the first column and the second column are axially disassembled from bulges and taken out from a lumen of the tissue, and then the plurality of bulges are taken out from the lumen.

17. The method for producing valved lumen shape tissue according to claim 16, wherein in the placement step, the base material for forming valved lumen shape tissue is placed in the environment, and a formation state of the tissue is observed by a body tissue formation observation apparatus while film-like tissue is being formed around the base material for forming valved lumen shape tissue;
wherein the base material further comprises, at an end of the first column, a body tissue formation observation apparatus including photographing means that photographs the leaflet forming section, and transmission means that transmits an image photographed by the photographing means to the outside of the environment with a body tissue material.

18. A valved artificial blood vessel formed with said base material of claim 1, said valved artificial blood vessel comprising:
a tubular section of a blood vessel, wherein said tubular section is formed by said first and/or second columns;
an ampulla with a blood vessel wall expanding radially outward, wherein said ampulla is formed by said outer peripheral surface; and
a leaflet that protrudes radially inward in the ampulla and is openable/closable in a blood flow direction, wherein said leaflet is formed by said gap,
wherein a thickness of the leaflet is 0.3 to 1.0 mm.

* * * * *